(12) United States Patent (10) Patent No.: US 8,124,623 B2
Hubschwerlen et al. (45) Date of Patent: Feb. 28, 2012

(54) 5-HYDROXYMETHYL-OXAZOLIDIN-2-ONE-DERIVATIVES AND THEIR USES AS ANTIBACTERIALS

(75) Inventors: Christian Hubschwerlen, Durmenach (FR); Hans Locher, Binningen (CH); Philippe Panchaud, Allschwil (CH); Jean-Luc Specklin, Kembs (FR)

(73) Assignee: Actelion Pharmaceuticals Ltd., Allschwil (CH)

( * ) Notice: Subject to any disclaimer, the term of this patent is extended or adjusted under 35 U.S.C. 154(b) by 266 days.

(21) Appl. No.: 12/463,281

(22) Filed: May 8, 2009

(65) Prior Publication Data
US 2009/0247578 A1 Oct. 1, 2009

Related U.S. Application Data

(63) Continuation-in-part of application No. PCT/IB2007/054557, filed on Nov. 9, 2007, and a continuation-in-part of application No. PCT/IB2008/051854, filed on May 9, 2008.

(30) Foreign Application Priority Data

Nov. 10, 2006 (WO) .................. PCT/IB2006/054189

(51) Int. Cl.
*A61K 31/04* (2006.01)
*C07D 215/38* (2006.01)
(52) U.S. Cl. .......................... 514/312; 546/153; 546/159
(58) Field of Classification Search .................. 546/159, 546/163; 514/312
See application file for complete search history.

(56) References Cited

U.S. PATENT DOCUMENTS

| | | | |
|---|---|---|---|
| 4,461,773 A | 7/1984 | Gregory | |
| 4,806,541 A | 2/1989 | Jolidon et al. | |
| 6,689,769 B2 * | 2/2004 | Gordeev et al. | 514/183 |
| 7,820,823 B2 * | 10/2010 | Hubschwerlen et al. | 546/153 |
| 2004/0132764 A1* | 7/2004 | Locher | 514/300 |

FOREIGN PATENT DOCUMENTS

| | | |
|---|---|---|
| EP | 0 216 345 | 4/1987 |
| JP | 04128288 | 9/1990 |
| KR | 2000-0067306 | 11/2000 |
| SU | 1156597 A | 5/1985 |
| WO | WO 88/07998 | 10/1988 |
| WO | WO 01/42242 | 6/2001 |
| WO | WO 02/59116 | 8/2002 |
| WO | WO 02/064574 | 8/2002 |
| WO | WO 03/031443 | 4/2003 |
| WO | WO 03/032962 | 4/2003 |
| WO | WO 03/064415 | 8/2003 |
| WO | WO 2004/096221 | 11/2004 |
| WO | WO 2005/023801 | 3/2005 |
| WO | 2005/058888 | * 6/2005 |
| WO | WO 2005/058886 | 6/2005 |
| WO | WO 2005/058888 | 6/2005 |
| WO | WO 2007/017828 | 2/2007 |
| WO | WO 2007/023507 | 3/2007 |
| WO | WO 2008/056335 | 5/2008 |

OTHER PUBLICATIONS

Eustice et al., Drugs Under Experimental and Clinical Research, vol. XVI, No. 4, pp. 149-155 (1990).
Gregory et al., Journal of Medicinal Chemistry, vol. 32, 1673-1681 (1989).
Written Opinion for International Application No. PCT/IB2007/054557, mailed Apr. 7, 2008.
Borredon, Tetrahedron Letters, vol. 28, No. 17, pp. 1877-1880, Great Britain, (1987).
Brickner, Current Pharmaceutical Design, vol. 2, pp. 175-194, (1996).
Corey et al., Journal of the American Chemical Society, vol. 87, No. 6, pp. 1353-1364, Dec. 1965.
Gennaro, A., Index from "Remington: The Science and Practice of Pharmacy", 20th Edition, Philadelphia College of Pharmacy and Science, (2001).
Gibson, M., Index from "Pharmaceutical Preformulation and Formulation", IHS Health Group, Englewood, GO, USA, ISBN: 1574911201, (2001).
Gould, P., "Salt Selection for Basic Drugs", International Journal of Pharmaceutics, vol. 33, pp. 201-217, Mar. 24, 1986.
Hamilton-Miller, Journal of Antimicrobial Chemotherapy, vol. 33, pp. 197-200, (1994).
Hubschwerlen et al., Bioorganic & Medicinal Chemistry Letters, vol. 13, pp. 4229-4233, Jul. 2003.

(Continued)

*Primary Examiner* — D M Seaman
(74) *Attorney, Agent, or Firm* — Hunton & Williams LLP

(57) ABSTRACT

The invention relates to novel chimeric antibiotics of formula I

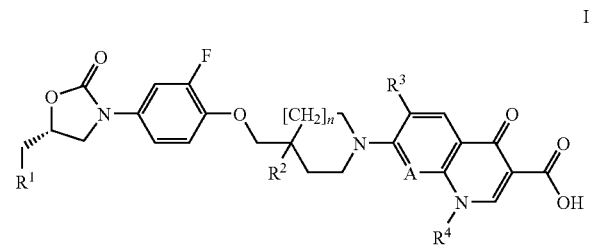

wherein
$R^1$ represents OH, $OPO_3H_2$ or $OCOR^5$;
$R^2$ represents H, OH or $OPO_3H_2$;
A represents N or $CR^6$;
$R^3$ represents H or fluorine;
$R^4$ is H, ($C_1$-$C_3$) alkyl, or cycloalkyl;
$R^5$ is the residue of a naturally occurring amino acid, of the enantiomer of a naturally occurring amino acid or of dimethylaminoglycine;
$R^6$ represents H, alkoxy or halogen; and
n is 0 or 1;
and to salts (in particular pharmaceutically acceptable salts) of compounds of formula I.
These chimeric compounds are useful in the manufacture of medicaments for the treatment of infections (e.g. bacterial infections).

18 Claims, 1 Drawing Sheet

OTHER PUBLICATIONS

Hubschwerlen et al., Bioorganic & Medicinal Chemistry, vol. 11, pp. 2313-2319, Jan. 2003.
Jacobsen et al., Journal of the American Chemical Society, vol. 110, pp. 1968-1970, Dec. 1987.
Kocienski, Protecting Groups, Foundations of Organic Chemistry Series—Thieme, (1994).
Mitsunobu, Synthesis—Reviews, vol. 1, pp. 1-28, Jan. 1981.
Sakurai, Bioorganic & Medicinal Chemistry Letters, vol. 8, pp. 2185-2190, Jul. 1998.
Vera-Cabrera et al., Antimicrobial Agents and Chemotherapy, vol. 50, No. 9, pp. 3170-3172, Sep. 2006.
International Search Report for International Application No. PCT/IB2007/054557 mailed Apr. 7, 2008.
Hubschwerlen et al. U.S. Appl. No. 12/063,305, filed Feb. 8, 2008.
Ranaldi et al. (1996) *Antimicrobial Agents and Chemotherapy* 40(3): 652-658.
Rudra et al. (2007) *Bioorganic & Medicinal Chemistry Letters* 17: 4778-4783.
Vera-Cabrera et al. (2006) *Antimicrobial Agents and Chemotherapy* 50(12): 4027-4029.
Yoon et al. (2005) *Antimicrobial Agents and Chemotherapy* 49(6): 2498-2500.

* cited by examiner

5-HYDROXYMETHYL-OXAZOLIDIN-2-ONE-DERIVATIVES AND THEIR USES AS ANTIBACTERIALS

CROSS-REFERENCE TO RELATED APPLICATIONS

This application is a continuation-in-part of PCT/IB2007/054557 with an international filing date of Nov. 9, 2007, which claims benefit of PCT/IB2006/054189 filed Nov. 10, 2006. This application is also a continuation-in-part of PCT/IB2008/051854 with an international filing date of May 9, 2008. Each of these documents are incorporated by reference herein.

FIELD OF THE INVENTION

The present invention concerns novel chimeric antibiotics that are obtained from oxazolidinone derivatives linked to a quinolone or naphthyridinone via a spacer, pharmaceutical antibacterial compositions containing them and the use of these compounds in the manufacture of a medicament for the treatment of infections (e.g. bacterial infections). These chimeric compounds are useful antimicrobial agents effective against a variety of human and veterinary pathogens including among others Gram-positive aerobic bacteria, Gram-negative bacteria, anaerobic organisms and acid-fast organisms.

BACKGROUND

The intensive use of antibiotics has exerted a selective evolutionary pressure on microorganisms to produce genetically based resistance mechanisms. Modern medicine and socio-economic behaviour exacerbate the problem of resistance development by creating slow growth situations for pathogenic microbes, e.g. in artificial joints, and by supporting long-term host reservoirs, e.g. in immuno-compromised patients.

In hospital settings, an increasing number of strains of *Staphylococcus aureus, Streptococcus pneumonia, Enterococcus* spp., and *Pseudomonas aeruginosa*, major sources of infections, are becoming multi-drug resistant and therefore difficult if not impossible to treat:

- *S. aureus* is β-lactam, quinolone and now even vancomycin resistant;
- *S. pneumoniae* is becoming resistant to penicillin, quinolone and even to new macrolides;
- Enteroccoci are quinolone and vancomycin resistant and β-lactams were never efficacious against these strains.

Further new emerging organisms like *Acinetobacter* spp. or *C. difficile*, which have been selected during therapy with the currently used antibiotics, are becoming a real problem in hospital settings.

In addition, microorganisms that are causing persistent infections are increasingly being recognized as causative agents or cofactors of severe chronic diseases like peptic ulcers or heart diseases.

In a chimeric molecule two or more molecules that exist separately in their native state are joined together to form a single entity (i.e. molecule) having the desired functionality of all of its constituent molecules.

Molecules wherein two antibiotics that have two different modes of action have been linked have been reported in the literature (e.g. *Journal of Antimicrobial Chemotherapy* (1994), 33, 197-200). Many of them are however such that the two antibiotic parts are released after biological activation (e.g. central ester cleavage, beta-lactam cleavage). Chemically and biochemically stable chimeric molecules that bind, as such, in two different targets have been more seldom reported. For example, oxazolidinone-quinolone hybrids have been reported as useful antimicrobial agents effective against a variety of multi-drug resistant pathogens (WO 03/032962, WO 03/031443 and WO 2004/096221, WO 2005/023801 and WO 2005/058888). Further, synthesis and biological evaluation of these hybrids (*Bioorg. & Med. Chem.* (2003), 11, 2313-2319) and the influence of the central spacer on the antibacterial activity in the structure-activity relationship in the oxazolidinone-quinolone series have also been reported (*Bioorg. Med. Chem. Lett.* (2003), 13, 4229-4233). All these derivatives contain a 4-aminomethyl-oxazolidinone rest as part of the oxazolidinone pharmacophore.

DETAILED DESCRIPTION OF PREFERRED EMBODIMENTS

Figure 1:
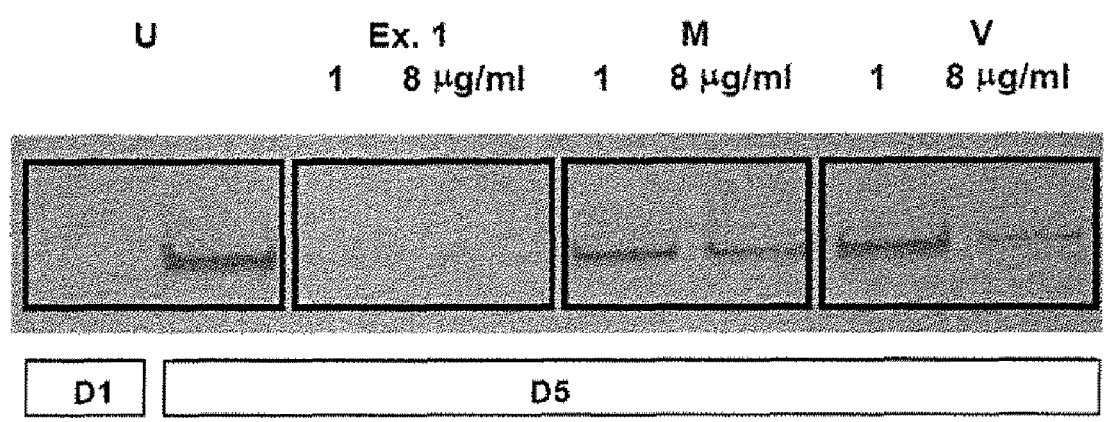
FIG. 1 shows the outlook of a Western Blot plate used in analyzing toxin A production in the supernatants of static high density cell cultures of *C. dfficile* NC 13366.

It has now been surprisingly found that the chimeric derivatives of formula I as defined hereafter are particularly effective antimicrobial agents that show effective against a variety of multi-drug resistant bacteria.

Thus, the present invention relates to compounds of formula I

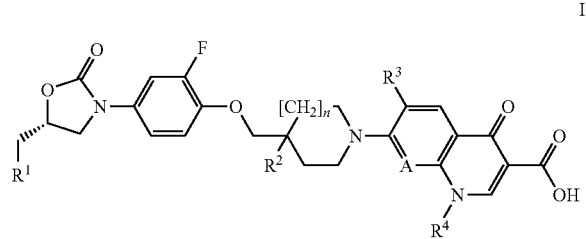

wherein
$R^1$ represents OH, $OPO_3H_2$ or $OCOR^5$;
$R^2$ represents H, OH or $OPO_3H_2$;
A represents N or $CR^6$;
$R^3$ represents H or fluorine;
$R^4$ is H, $(C_1$-$C_3)$ alkyl or cycloalkyl;
$R^5$ is the residue of a naturally occurring amino acid, of the enantiomer of a naturally occurring amino acid or of dimethylaminoglycine;
$R^6$ represents H, alkoxy or halogen; and
n is 0 or 1;
and to salts (in particular pharmaceutically acceptable salts) of compounds of formula I.

The compounds of formula I may contain one or more stereogenic or asymmetric centers, such as one or more asymmetric carbon atoms. The compounds of formula I may thus be present as mixtures of stereoisomers or preferably as pure stereoisomers. Mixtures of stereoisomers may be separated in a manner known to a person skilled in the art. The following paragraphs provide definitions of the various chemical moieties for the compounds according to the invention and are intended to apply uniformly throughout the specification and claims unless an otherwise expressly set out definition provides a broader or narrower definition.

Unless specified otherwise, the term "alkyl" (whether used alone or in combination) refers to a saturated straight or branched chain alkyl group containing 1 to 6 carbon atoms, and preferably 1 to 3 carbon atoms. Representative examples of alkyl groups include, but are not limited to, methyl, ethyl, propyl, iso-propyl, butyl, iso-butyl, sec-butyl, tert-butyl, n-pentyl, neopentyl, iso-pentyl, n-hexyl and iso-hexyl. The term "$(C_1$-$C_x)$alkyl" (x being an integer) refers to a saturated straight or branched chain alkyl group containing 1 to x carbon atoms.

The term "alkoxy" refers to a saturated straight or branched chain alkoxy group, containing 1 to 6 carbon atoms, and preferably 1 to 3 carbon atoms. Representative examples of alkoxy groups include, but are not limited to, methoxy, ethoxy, propoxy, iso-propoxy, n-butoxy, iso-butoxy, sec-butoxy, tert-butoxy or n-hexyloxy. The term "$(C_1$-$C_x)$alkoxy" (x being an integer) refers to a straight or branched chain alkoxy group containing 1 to x carbon atoms.

The term "halogen" refers to fluorine, chlorine, bromine or iodine, and preferably to fluorine or chlorine.

The term "cycloalkyl", used alone or in combination, refers to a saturated cyclic hydrocarbon moiety containing 3 to 6 carbon atoms and preferably 3 to 5 carbon atoms. Representative examples of cycloalkyl groups include, but are not limited to, cyclopropyl and cyclopentyl.

When it is written that $R^5$ is the residue of an amino acid, it is meant thereby that $R^5$—COOH is the corresponding amino acid.

The term "pharmaceutically acceptable salts" refers to non-toxic, inorganic or organic acid and/or base addition salts, Reference can be made to "Salt selection for basic drugs", *Int. J. Pharm.* (1986), 33, 201-217.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.; besides, room temperature shall mean in the current patent application 25° C.

In particular, the invention relates to compounds of formula I that are also compounds of formula $I_{CE}$

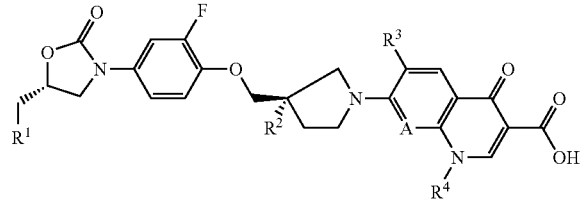

wherein
$R^1$ represents OH, $OPO_3H_2$ or $OCOR^5$;
$R^2$ represents H, OH or $OPO_3H_2$;
A represents N or $CR^6$;
$R^3$ represents fluorine;
$R^4$ represents H, $(C_1$-$C_3)$ alkyl or cycloalkyl;
$R^5$ is the residue of a naturally occurring amino acid (in particular the residue of Ala);
$R^6$ represents H or alkoxy; and
n is 0 or 1;
and to salts (in particular pharmaceutically acceptable salts) of compounds of formula $I_{CE}$.

According to a first main embodiment of this invention, the compounds of formula I are such that n is 0. Such compounds will be hereafter referred to as "compounds of formula $I_5$".

According to one particular variant of the first main embodiment, the compounds of formula $I_5$ will be such that they have the following stereochemistry:

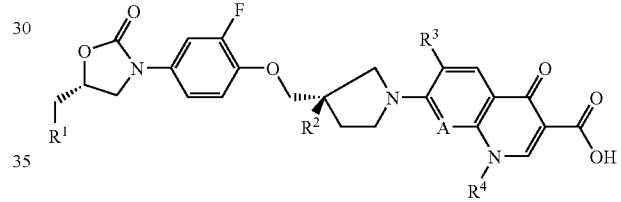

According to another variant of the first main embodiment, the compounds of formula $I_5$ will be such that they have the following stereochemistry:

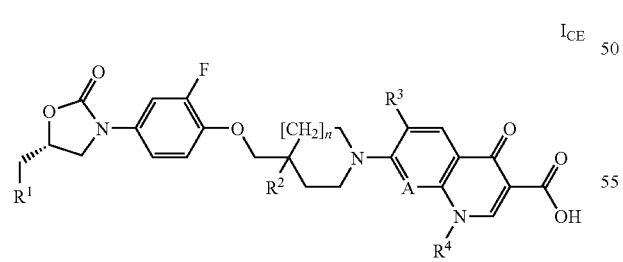

According to a second main embodiment of this invention, the compounds of formula I are such that n is 1. Such compounds will be hereafter referred to as "compounds of formula $I_6$".

According to a further main embodiment of this invention, the compounds of formula I will be such that they are also compounds of formula $I_D$ wherein
$R^2$ represents H or OHl;
A represents N or $CR^6$;
$R^3$ represents fluorine;
$R^4$ represents H, $(C_1$-$C_3)$ alkyl or cycloalkyl;
$R^6$ represents H or alkoxy; and
n is 0 or 1.

According to yet another main embodiment of this invention, the compounds of formula I will be such that they are also compounds of formula $I_{PDG}$

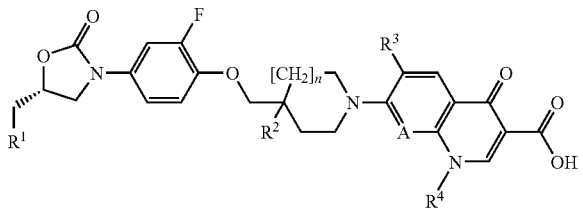

wherein
$R^1$ represents OH and $R^2$ represents $OPO_3H_2$, or $R^1$ represents $OPO_3H_2$ or $OCOR^5$ and
$R^2$ represents H, OH or $OPO_3H_2$;
A represents N or $CR^6$;
$R^3$ represents fluorine,
$R^4$ represents H, $(C_1-C_3)$ alkyl or cycloalkyl;
$R^5$ is the residue of a naturally occurring amino acid (in particular the residue of Ala);
$R^6$ represents H or alkoxy; and
n is 0 or 1.

According to a particular embodiment of this invention, the compounds of formula I will be such that A represents N.

According to another particular embodiment of this invention, the compounds of formula I will be such that A represents $CR^6$. In such case, $R^6$ will preferably represent H or alkoxy (and in particular H or methoxy).

According to an important variant of this invention, the compounds of formula I will be such that $R^1$ is OH.

According to another important variant of this invention, the compounds of formula I will be such that $R^1$ is $OPO_3H_2$ or $OCOR^5$.

According to yet another important variant of this invention, the compounds of formula I will be such that $R^1$ is H.

According to yet another important variant of this invention, the compounds of formula I will be such that $R^2$ is OH.

According to a further important variant of this invention, the compounds of formula I will be such that $R^2$ is $OPO_3H_2$.

Preferably, the amino acid residue $R^5$ is such that $R^5$—COOH represents a natural amino acid (notably Ala).

Preferred compounds of formula I are also those wherein at least one of the following characteristics is present:
A represents $CR^6$;
$R^1$ represents OH or $OPO_3H_2$;
$R^2$ represents H or OH;
$R^3$ represents fluorine;
$R^4$ represents $(C_1-C_3)$alkyl or cycloalkyl.

More preferred compounds of formula I are those wherein at least one of the following characteristics is present:
n is 0;
A represents $CR^6$, $R^6$ representing H or alkoxy (and preferably H or methoxy);
$R^1$ represents OH;
$R^2$ represents H or OH;
$R^3$ represents fluorine;
$R^4$ represents cycloalkyl.

Even more preferred compounds of formula I are those wherein at least one of the following characteristics is present:
n is 0;
A represents $CR^6$, $R^6$ representing H or methoxy;
$R^1$ represents OH;
$R^2$ represents H or OH (and notably OH);
$R^3$ represents fluorine;
$R^4$ represents $(C_3-C_5)$cycloalkyl (and in particular cyclopropyl).

The following compounds of formula I are particularly preferred.

1-cyclopropyl-6-fluoro-7-{4-[2-fluoro-4-((R)-5-hydroxymethyl-2-oxo-oxazolidin-3-yl)-phenoxymethyl]-4-hydroxy-piperidin-1-yl}-4-oxo-1,4-dihydro-quinoline-3-carboxylic acid;

1-cyclopropyl-6-fluoro-7-{4-[2-fluoro-4-((R)-5-hydroxymethyl-2-oxo-oxazolidin-3-yl)-phenoxymethyl]-piperidin-1-yl}-4-oxo-1,4-dihydro-quinoline-3-carboxylic acid;

1-cyclopropyl-6-fluoro-7-{4-[2-fluoro-4-((R)-5-hydroxymethyl-2-oxo-oxazolidin-3-yl)-phenoxymethyl]-4-hydroxy-piperidin-1-yl}-4-oxo-1,4-dihydro-[1,8]naphthyridine-3-carboxylic acid;

7-(4-{4-[(R)-5-((S)-2-amino-propionyloxymethyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid;

1-cyclopropyl-6-fluoro-7-{4-[2-fluoro-4-((R)-2-oxo-5-phosphonooxymethyl-oxazolidin-3-yl)-phenoxymethyl]-4-hydroxy-piperidin-1-yl}-4-oxo-1,4-dihydro-quinoline-3-carboxylic acid;

1-cyclopropyl-6-fluoro-7-{(R)-3-[2-fluoro-4-((R)-5-hydroxymethyl-2-oxo-oxazolidin-3-yl)-phenoxymethyl]-3-hydroxy-pyrrolidin-1-yl}-4-oxo-1,4-dihydro-quinoline-3-carboxylic acid;

1-cyclopropyl-6-fluoro-7-{(S)-3-[2-fluoro-4-((R)-5-hydroxymethyl-2-oxo-oxazolidin-3-yl)-phenoxymethyl]-3-hydroxy-pyrrolidin-1-yl}-4-oxo-1,4-dihydro-quinoline-3-carboxylic acid;

1-cyclopropyl-6-fluoro-7-{(R)-3-[2-fluoro-4-((R)-5-hydroxymethyl-2-oxo-oxazolidin-3-yl)-phenoxymethyl]-3-hydroxy-pyrrolidin-1-yl}-8-methoxy-4-oxo-1,4-dihydro-quinoline-3-carboxylic acid;

1-cyclopropyl-6-fluoro-7-{(S)-3-[2-fluoro-4-((R)-5-hydroxymethyl-2-oxo-oxazolidin-3-yl)-phenoxymethyl]-3-hydroxy-pyrrolidin-1-yl}-8-methoxy-4-oxo-1,4-dihydro-quinoline-3-carboxylic acid;

1-cyclopropyl-6-fluoro-7-{(R)-3-[2-fluoro-4-((R)-5-hydroxymethyl-2-oxo-oxazolidin-3-yl)-phenoxymethyl]-pyrrolidin-1-yl}-4-oxo-1,4-dihydro-quinoline-3-carboxylic acid;

1-cyclopropyl-6-fluoro-7-{(S)-3-[2-fluoro-4-((R)-5-hydroxymethyl-2-oxo-oxazolidin-3-yl)-phenoxymethyl] pyrrolidin-1-yl}-4-oxo-1,4-dihydro-quinoline-3-carboxylic acid;

1-cyclopropyl-6-fluoro-7-{(R)-3-[2-fluoro-4-((R)-5-hydroxymethyl-2-oxo-oxazolidin-3-yl)-phenoxymethyl]-pyrrolidin-1-yl}-8-methoxy-4-oxo-1,4-dihydro-quinoline-3-carboxylic acid;

1-cyclopropyl-6-fluoro-7-{(S)-3-[2-fluoro-4-((R)-5-hydroxymethyl-2-oxo-oxazolidin-3-yl)-phenoxymethyl]-pyrrolidin-1-yl}-8-methoxy-4-oxo-1,4-dihydro-quinoline-3-carboxylic acid;

1-cyclopropyl-6-fluoro-7-{4-[2-fluoro-4-((R)-5-hydroxymethyl-2-oxo-oxazolidin-3-yl)-phenoxymethyl]-4-phosphonooxy-piperidin-1-yl}-4-oxo-1,4-dihydro-quinoline-3-carboxylic acid;

1-ethyl-6-fluoro-7-{4-[2-fluoro-4-((R)-5-hydroxymethyl-2-oxo-oxazolidin-3-yl)-phenoxymethyl]-piperidin-1-yl}-4-oxo-1,4-dihydro-quinoline-3-carboxylic acid;

7-(4-{4-[(R)-5-((S)-2-amino-propionyloxymethyl)-2-oxo-oxazolidin-3-yl]-2-fluoro-phenoxymethyl}-piperidin-1-yl)-1-cyclopropyl-6-fluoro-4-oxo-1,4-dihydro-quinoline-3-carboxylic acid;

6-fluoro-7-{4-[2-fluoro-4-((R)-5-hydroxymethyl-2-oxo-oxazolidin-3-yl)-phenoxymethyl]-4-hydroxy-piperidin-1-yl}-4-oxo-1,4-dihydro-quinoline-3-carboxylic acid;

6-fluoro-7-{4-[2-fluoro-4-((R)-5-hydroxymethyl-2-oxo-oxazolidin-3-yl)-phenoxymethyl]-4-hydroxy-piperidin-1-yl}-4-oxo-1,4-dihydro-[1,8]naphthyridine-3-carboxylic acid; as well as salts thereof (and in particular pharmaceutically acceptable salts thereof).

Chimeric derivatives of formula I are suitable for the use as medicaments, particularly as antimicrobial agents, in human medicine but also in veterinary medicine in the treatment of species like pigs, ruminants, horses, dogs, cats and poultry.

Chimeric derivatives of formula I according to the present invention are also useful for the manufacture of a medicament for the treatment of infections (notably bacterial infections or protozoal infections) and disorders related to infections (notably disorders related to bacterial infections or to protozoal infections).

The compounds according to this invention are particularly active against bacteria and bacteria-like organisms. They are therefore particularly suitable in human, as well as in animals, for the prophylaxis and chemotherapy of local and systemic infections caused by these pathogens as well as disorders related to bacterial infections comprising pneumonia, otitis media, sinusitis, bronchitis, tonsillitis, and mastoiditis related to infection by *Streptococcus pneumoniae, Haemophilus influenzae, Moraxella catarrhalis, Staphylococcus aureus, Enterococcus faecalis, F. faecium, E. casselifavus, S. epidermidis, S. haemolyticus*, or *Peptostreptococcus* spp.; pharyngitis, rheumatic fever, and glomerulonephritis related to infection by *Streptococcus pyogenes*, Groups C and *G. streptococci, Corynebacterium diphtheriae*, or *Actinobacillus haemolyticuim*; respiratory tract infections related to infection by *Mycoplasma pneumoniae, Legionella pneumophila, Streptococcus pneumoniae, Haemophilus influenzae*, or *Chlamydia pneumoniae*; blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracyclines and macrolides; uncomplicated skin and soft tissue infections and abscesses, and puerperal fever related to infection by *Staphylococcus aureus*, coagulase-negative staphylococci (i.e., *S. epidermidis, S. haemolyticus*, etc.), *Streptococcus pyogenes, Streptococcus agalactiae*, Streptococcal groups C-F (minute colony streptococci), viridans streptococci, *Corynebacterium minutissimum, Clostridium* spp., or *Bartonella henselae*; uncomplicated acute urinary tract infections related to infection by *Staphylococcus aureus*, coagulase-negative staphylococcal species, or *Enrerococcus* spp.; urethritis and cervicitis; sexually transmitted diseases related to infection by *Chlamydia trachomatis, Haemophilus ducreyi, Treponema pallidum, Ureaplasma urealyticum*, or *Neiserria gonorrhoeae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae*, or *Listeria* spp.; disseminated *Mycobacteriuim avium* complex (MAC) disease related to infection by *Mycobacterium avium*, or *Mycobacterium intracellulare*; infections caused by *Mycobacterium tuberculosis, M. leprae, M. paratuberculosis, M. kansasii*, or *M. chelonei*; gastroenteritis related to infection by *Campylobacter jejuni*; intestinal protozoa related to infection by *Cryprosporidium* spp.; odontogenic infection related to infection by viridans streptococci; persistent cough related to infection by *Bordetella pertussis*; gas gangrene related to infection by *Clostridium perfringens* or *Bacteroides* spp.; and atherosclerosis or cardiovascular disease related to infection by *Helicobacter* pylorn or *Chlamydia pneumoniae*.

Compounds of formula I according to the present invention are further useful for the preparation of a medicament for the treatment of infections that are mediated by bacteria such as *E. coli, Klebsiella pneumoniae* and other Enterobacteriaceae, *Acinetobacter* spp., *Stenothrophomonas nialtophila, Neisseria meningitidis, Bacillus cereus, Bacillus anthracis, Corynebacterium* spp., *Propionibacterium acnes* and bacteroide spp. In addition, compounds of formula I according to the present invention are further useful for the preparation of a medicament for the treatment of infections that are mediated by *Clostridim difficile*.

Compounds of formula I according to the present invention are further useful to treat protozoal infections caused by *Plasmodium malaria, Plasmodiu falciparum, Toxoplasma gondii, Pneamocystis carinli, Trypanosoma brucei* and *Leishmania* spp.

The preceding lists of pathogens are to be interpreted merely as examples and in no way as limiting.

As well as in humans, bacterial infections can also be treated in other species like pigs, ruminants, horses, dogs, cats and poultry.

Therefore, the compounds of formula I or their pharmaceutically acceptable salts can be used for the preparation of a medicament, and are suitable, for the prevention or treatment of bacterial infections (notably those caused by the pathogens mentioned in the lists above).

The compounds of formula I and their pharmaceutically acceptable salts can be used as medicaments, e.g. in the form of pharmaceutical compositions for enteral or parental administration.

The production of the pharmaceutical compositions can be effected in a manner which will be familiar to any person skilled in the art (see for example Mark Gibson, Editor, Pharmaceutical Preformulation and Formulation, IHS Health Group, Englewood, Colo., USA, 2001; Remington, *The Science and Practice of Pharmacy*, 20th Edition, Philadelphia College of Pharmacy and Science) by bringing the described compounds of formula I or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Another aspect of the invention concerns a method for the treatment of an infection comprising the administration to the patient of a pharmaceutically active amount of a compound according to formula I or of a pharmaceutically acceptable salt thereof.

Moreover, the compounds of formula I may also be used for cleaning purposes, e.g. to remove pathogenic microbes and bacteria from surgical instruments or to make a room or an area aseptic. For such purposes, the compounds of formula I could be contained in a solution or in a spray formulation.

Any reference to a compound of formula I, $I_{S1}$, $I_{S2}$, $I_6$, $I_D$ or $I_{PDG}$ is to be understood as referring also to a salt (especially a pharmaceutically acceptable salt) of a compound of formula I, $I_{S1}$, $I_{S2}$, $I_6$, $I_D$ or $I_{PDC}$ respectively, as appropriate and expedient. Besides, any preferences indicated for the compounds of formula I (whether for the compounds themselves, salts thereof, compositions containing the compounds or salts thereof, uses of the compounds or salts thereof etc.) apply *mutatis mutandis* to compounds of formula I$_{CE}$, the compounds of formula I$_5$, the compounds of formula I$_{51}$, the compounds of formula I$_{52}$, the compounds of formula I$_6$, the compounds of formula I$_D$ and the compounds of formula I$_{PDG}$.

Various additional embodiments of the invention are presented hereafter:

i) According to its first additional embodiment, the present invention relates to the compounds of formula I$_{INT}$

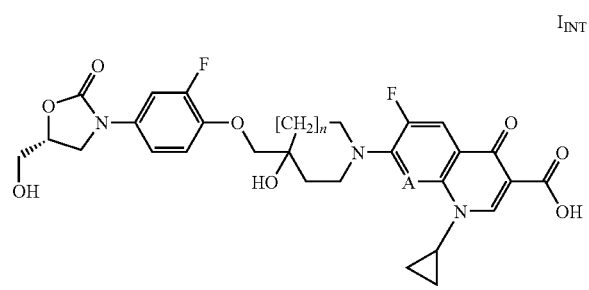

I$_{INT}$ wherein
A is N or CH; and
n is 0 or 1;
or the pharmaceutically acceptable salts thereof, for preventing or treating intestinal diseases which are caused by bacteria selected from *Clostridium difficile, Clostridium perfringens* or *Staphylococcus aureus*.

The following paragraphs provide additional definitions of various terms used in the additional embodiments and are intended to apply uniformly throughout said additional embodiments and the corresponding claims unless an otherwise expressly set out definition provides a broader or narrower definition.

The term "preventing", "prevent" or "prevention" used with reference to a disease means either that said disease does not occur in the patient or animal, or that, although the animal or patient is affected by the disease, part or all the symptoms of the disease are either reduced or absent.

The term "treating", "treat" or "treatment" used with reference to a disease means either that said disease is cured in the patient or animal, or that, although the animal or patient remains affected by the disease, part or all the symptoms of the disease are either reduced or eliminated.

ii) Preferably, the compound of formula I$_{INT}$ as defined in embodiment i), or a pharmaceutically acceptable salt thereof, will allow effective prevention or treatment of diarrhea diseases associated with enterotoxigenic strains of *Clostridium difficile, Clostridium perfringens* or *Staphylococcus aureus* without increasing the concentration of vancomycin-resistant enterococci (VRE) in the gut.

iii) More preferably, the compound of formula I$_{INT}$ as defined in embodiment i), or a pharmaceutically acceptable salt thereof, will allow effective prevention or treatment of diarrhea diseases associated with enterotoxigenic strains of *Clostridium difficile, Clostridium perringens* or *Staphylococcus aureus* and reduction of the concentration of VRE in the gut.

iv) Preferably, the compounds of formula INT as defined in one of embodiments i) to iii), or the pharmaceutically acceptable salts thereof will be such that A is CH.

v) Preferably also, the compounds of formula I$_{INT}$ as defined in one of embodiments i) to iv), or the pharmaceutically acceptable salts thereof, will be such that n is 1.

vi) According to preferred sub-embodiments of embodiments i) to iii), the compound of formula I$_{INT}$ or its pharmaceutically acceptable salt will be selected from:

1-cyclopropyl-6-fluoro-7-{4-[2-fluoro-4-((R)-5-hydroxymethyl-2-oxo-oxazolidin-3-yl)-phenoxymethyl]-4-hydroxy-piperidin-1-yl}-4-oxo-1,4-dihydro-quinoline-3-carboxylic acid;

1-cyclopropyl-6-fluoro-7-{4-[2-fluoro-4-((R)-5-hydroxymethyl-2-oxo-oxazolidin-3-yl)-phenoxymethyl]-4-hydroxy-piperidin-1-yl}-4-oxo-1,4-dihydro-[1,8]naphthyridine-3-carboxylic acid;

1-cyclopropyl-6-fluoro-7-{3-[2-fluoro-4-((R)-5-hydroxymethyl-2-oxo-oxazolidin-3-yl)-phenoxymethyl]-3-hydroxy-pyrrolidin-1-yl}-4-oxo-1,4-dihydro-quinoline-3-carboxylic acid;

and the pharmaceutically acceptable salts thereof.

vii) According to more preferred sub-embodiments of embodiments i) to iii), the compound of formula I$_{INT}$ or its pharmaceutically acceptable salt will be 1-cyclopropyl-6-fluoro-7-{4-[2-fluoro-4-((R)-5-hydroxymethyl-2-oxo-oxazolidin-3-yl)-phenoxymethyl]-4-hydroxy-piperidin-1-yl}-4-oxo-1,4-dihydro-quinoline-3-carboxylic acid or a pharmaceutically acceptable salt thereof.

viii) According to one aspect of embodiments i) to vii), the present invention will relate to the compounds of formula I$_{INT}$ as defined in one of embodiments i) to vii), or the pharmaceutically acceptable salts thereof, for treating the intestinal diseases which are caused by bacteria selected from *Clostridium difficile, Clostridium pefringens* and *Staphylococcus aureus*.

ix) According to one preferred aspect of embodiment viii), the present invention will relate to the compounds of formula I$_{INT}$ as defined in one of embodiments i) to vii), or the pharmaceutically acceptable salts thereof, for treating the intestinal diseases which are caused by *Clostridium difficile* (notably by a toxin producing strain of *Clostridium difficile*).

x) According to another main aspect of embodiments i) to vii), the present invention will relate to the compounds of formula I$_{INT}$ as defined in one of embodiments i) to vii), or the pharmaceutically acceptable salts thereof, for preventing the intestinal diseases which are caused by bacteria selected from *Clostridium difficile, Clostridium perfringens* and *Staphylococcus aureus*.

xi) According to one preferred aspect of embodiment x), the present invention will relate to the compounds of formula I$_{INT}$ as defined in one of embodiments i) to vii), or the pharmaceutically acceptable salts thereof, for preventing the intestinal diseases which are caused by *Clostridium difficile* (notably by a toxin producing strain of *Clostridium difficile*).

xii) Preferably, the patients in which the intestinal diseases mentioned in embodiments i) to xi) are intended to be prevented will be patients treated with other antibiotics or with antiviral therapies, patients with an immunocompromised system such as cytotoxic chemotherapy or organ transplant patients, elderly (65 years or older) patients, or patients of intensive care units or of long-term care facilities.

xiii) Yet another main embodiment of this invention relates to a method of preventing or treating in a patient an intestinal disease which is caused by bacteria selected from *Clostridium difficile, Clostridium perfringens* and *Staphylococcus aureus*, said method comprising the administration to said patient of an effective amount of a compound of formula I$_{INT}$ as defined in one of embodiments i) to vii), or of a pharmaceutically acceptable salt of such a compound, for a duration sufficient to prevent or treat the intestinal disease.

xiv) Preferably, the method of embodiment xiii) will allow effective prevention or treatment of diarrhea diseases associated with enterotoxigenic strains of *Clostridium difficile, Clostriditem perfringens* or *Staphylococcus agreus* without increasing the concentration of vancomycin-resistant enterococci (VRE) in the gut.

xv) More preferably, the method of embodiment xiii) will allow effective prevention or treatment of diarrhea diseases associated with enterotoxigenic strains of *Clostridium dfficile, Clostridiun peifringens* or *Staphylococcus aureus* and reduction of the concentration of VRE in the gut.

xvi) According to one aspect of embodiments xiii) to xv), the present invention will relate to a method of treating in a patient an intestinal disease which is caused by bacteria selected from *Clostridium difficile, Clostridium perfringens* and *Staphylococcus aureus*, said method comprising the administration to said patient of an effective amount of a compound of formula $I_{INT}$ as defined in one of embodiments i) to vii), or of a pharmaceutically acceptable salt of such a compound, for a duration sufficient to treat the intestinal disease.

xvii) According to one preferred aspect of embodiment xvi), the present invention will relate to a method of treating in a patient an intestinal disease which is caused by *Clostridium difficile* (notably by a toxin producing strain of *Clostridium difficile*).

xviii) According to another aspect of embodiments xiii) to xv), the present invention will relate to a method of preventing in a patient an intestinal disease which is caused by bacteria selected from *Clostridium dfficile, Clostridium perfringens* and *Staphylococcus aureus*, said method comprising the administration to said patient of an effective amount of a compound of formula $I_{INT}$ as defined in one of embodiments i) to vii), or of a pharmaceutically acceptable salt of such a compound, for a duration sufficient to prevent the intestinal disease.

xix) According to one preferred aspect of embodiment xviii), the present invention will relate to a method of preventing in a patient an intestinal disease which is caused by *Clostridium difficile* (notably by a toxin producing strain of *Clostridium* dfficile).

xx) Preferably, the patients subjected to a method of one of embodiments xiii) to xix) will be patients treated with other antibiotics or with antiviral therapies, patients with an immunocompromised system such as cytotoxic chemotherapy or organ transplant patients, elderly (65 years or older) patients, or patients of intensive care units or of long-term care facilities.

xxi) Yet a further aspect of this invention relates to the use of a compound of formula $I_{INT}$ as defined in one of embodiments i) to vii), or of a pharmaceutically acceptable salt of such a compound, for the manufacture of a medicament intended to prevent or treat an intestinal disease which is caused by bacteria selected from *Clostridium difficile, Clostridium perfringens* and *Stapkylococcus aureus*.

xxii) According to one aspect of embodiment xxi), the present invention will relate to the use of a compound of formula $I_{INT}$ as defined in one of embodiments i) to vii), or of a pharmaceutically acceptable salt of such a compound, for the manufacture of a medicament intended to treat an intestinal disease which is caused by bacteria selected from *Clostridium difficile, Clostridiur perfringens* and *Staphylococcus aureus*.

xxiii) According to one preferred aspect of embodiment xxii), the intestinal disease intended to be treated will be caused by *Clostridium difficile* (notably by a toxin producing strain of *Clostridium difficile*).

xxiv) According to another aspect of embodiment xxi), the present invention will relate to the use of a compound of formula $I_{INT}$ as defined in one of embodiments i) to vii), or of a pharmaceutically acceptable salt of such a compound, for the manufacture of a medicament intended to prevent an intestinal disease which is caused by bacteria selected from *Clostridium difficile, Clostridium perfringens* and *Staphylococcus aureus*.

xxv) According to one preferred aspect of embodiment xxiv), the intestinal disease intended to be prevented will be caused by *Clostridium difficile* (notably by a toxin producing strain of *Clostridium difficile*).

xxvi) Preferably, the patients for which the medicament manufactured according to one of embodiments xxi) to xxv) will be intended will be patients treated with other antibiotics or with antiviral therapies, patients with an immunocompromised system such as cytotoxic chemotherapy or organ transplant patients, elderly (65 years or older) patients, or patients of intensive care units or of long-term care facilities.

xxvii) Another aspect of this invention relates to a method of preventing or treating in an animal (e.g. in a dog, a cat, a pig, a cow or a horse) an intestinal disease caused by bacteria selected from *Clostridium difficile, Clostridium perfringens* and *Staphylococcus aureus*, said method comprising the administration to said animal of an effective amount of a compound of formula $I_{INT}$ as defined in one of embodiment i) to vii), or of a pharmaceutically acceptable salt of such a compound, for a duration sufficient to treat the intestinal disease.

xxviii) According to one aspect of embodiment xxvii), the present invention will relate to a method of treating in an animal (e.g. in a dog, a cat, a pig, a cow or a horse) an intestinal disease which is caused by bacteria selected from *Clostridium difficile, Clostridium peifringens* and *Staphylococcus aureus*, said method comprising the administration to said patient of an effective amount of a compound of formula $I_{INT}$ as defined in one of embodiments i) to vii), or of a pharmaceutically acceptable salt of such a compound, for a duration sufficient to treat the intestinal disease.

xxix) According to another aspect of embodiment xxvii), the present invention will relate to a method of preventing in an animal (e.g. in a dog, a cat, a pig, a cow or a horse) an intestinal disease which is caused by bacteria selected from *Clostridium difficile, Clostridium perfringens* and *Staphlylococcus aureus*, said method comprising the administration to said patient of an effective amount of a compound of formula I as defined in one of embodiments i) to vii), or of a pharmaceutically acceptable salt of such a compound, for a duration sufficient to prevent the intestinal disease.

The intestinal diseases intended to be prevented or treated according to embodiments i) to xxix) of this invention comprise notably diarrhea, colitis and pseudomembranous colitis. Preferably, said intestinal diseases will be caused by *Clostridium difficile* (and especially by a toxin producing strain of *Clostridium difficile*).

The most suitable administration route for the compounds of formula $I_{INT}$ used according to embodiments i) to xxix) of the present invention will be the oral route. Administration may be daily (e.g., one to four times daily) or may be less frequent (e.g., once every other day or once or twice weekly).

Though the exact administration doses of a compound of formula $I_{INT}$ as defined in one of embodiments i) to vii), or of a pharmaceutically acceptable salt thereof, will have to be determined by the treating physician or veterinarian, it is expected that an amount between 0.5 and 50 mg of compound of formula $I_{INT}$ or pharmaceutically acceptable salt thereof per kg of patient body weight per day (for example an amount between 1 and 5 mg of compound of formula $I_{INT}$ or pharmaceutically acceptable salt thereof per kg of patient body weight per day) given once or twice daily for a duration of 3 to 15 days (for example for a duration of 7 to 14 days) will be appropriate.

According to the invention, the compounds of formula I can be prepared by the process described hereafter.

Preparation of the Compounds of Formula I

Abbreviations:

The following abbreviations are used throughout the specification and the examples:

AcOH acetic acid
AD-mix α 1,4-bis(dihydroquinine)phthalazine, $K_3Fe(CN)_6$, $K_2CO_3$ and $K_2OSO_4.2H_2O$
AD-mix β 1,4-bis(dihydroquilnidine)phthalazine, $K_3Fe(CN)_6$, $K_2CO_3$ and $K_2OSO_4.2H_2O$
Alloc allyloxycarbonyl
aq. aqueous
BnBr benzyl bromide
Boc tert-butoxycarbonyl
t-BuOK potassium tert-butylate
Cbz benzyloxycarbonyl
DBU 1,8-diazabicyclo[5.4.0]undec-7-ene
DCM dichloromethane
DIAD diisopropyl azodicarboxylate
DIPEA N,N-diisopropylethylamine
DMA dimethylacetamide
DMAP 4-dimethylaminopyridine
DMF N,N-dimethylformamide
DMSO dimethylsulfoxide
EA ethyl acetate
EDC 1-(dimethylaminopropyl)-3-ethylcarbodiimide hydrochloride
ESI Electron Spray Ionisation
ether or $Et_2O$ diethyl ether
FC flash chromatography
h hour
Hex n-hexane
IC50 concentration that reduces the effect by 50%
MeCN acetonitrile
MCPBA meta-chloroperbenzoic acid
MheOH methanol
MIC90 minimal inhibitory concentration to inhibit the growth of ≧90% of strains
MS Mass Spectroscopy
NaOMe sodium methylate
NMP N-methylpyrrolidinone
$OD_{595}$ optical density measured at 595 nM
org. organic
Pd/C or $Pd(OH)_2$/C palladium or dihydroxypalladium on charcoal
$PPh_3$ kiphenylphosphine
rt room temperature
sat. saturated
$SiO_2$ silica gel
TBDMSCl tert-butyldimethylsilyl chloride
TEA triethylamine
TFA trifluoroacetic acid
THF tetrahydrofuran
TMSCl trimethylsilyl chloride General Preparation Routes:

The novel compounds of formula I can be manufactured in accordance with the present invention by a) reacting the compound of formula TI

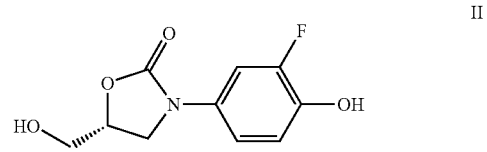

with a compound of formula III

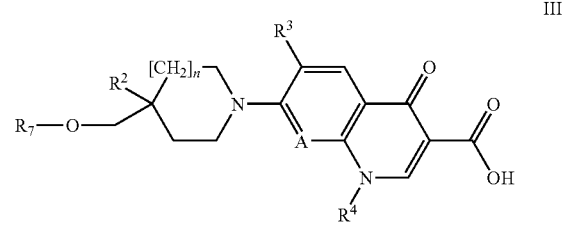

wherein n, A, $R^3$ and $R^4$ are as defined in formula I and $R^7$ is ($C_1$-$C_3$)alkylsulfonyl (e.g. methylsulfonyl), trifluoromethylsulfonyl or arylsulfonyl (e.g. phenyl- or p-tolyl-sulfonyl) and R is OH or H, or $R^2$ and $R^7$ together form a bond (i.e. $R^2$ and $OR^7$ form, together with the carbon atoms that carry them, an epoxide ring), preferably between about 10° C. and 100° C. (more preferably between about 40° C. and 80° C.), in the presence of an inorganic base such as $K_2CO_3$ or an organic base such as TEA in an organic solvent (e.g. DMF);

or b) reacting a compound of formula IV

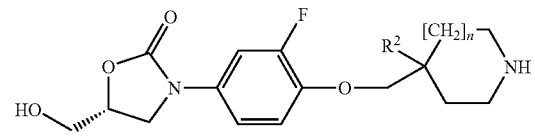

wherein n is as defined in formula I and $R^2$ is H or OH, with a compound of formula V

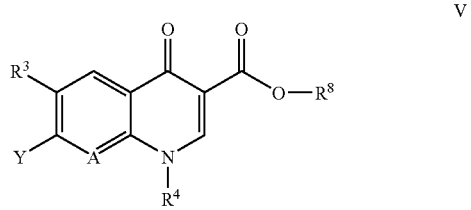

wherein A, $R^3$ and $R^4$ are as defined in formula I, Y is halogen and $R^8$ is hydrogen, $BF_2$ or $B(OC(=O)(C_1$-$C_4)$ alkyl)$_2$, ($C_1$-$C_5$)alkyl (e.g. methyl, ethyl, n-propyl, isopropyl or tert-butyl), allyl, aryl-($C_1$-$C_5$)alkyl (e.g. benzyl, p-nitrobenzyl or p-methoxybenzyl), tri-($C_1$-$C_5$)

alkylsilyl (e.g. trimethylsilyl or tert-butyldimethylsilyl) or diaryl-(C₁-C₅)alkylsilyl (e.g. rert-butyldiphenylsilyl), preferably between about 10° C. and 100° C., more preferably between about 40° C. and 80° C. in the presence of an organic base, such as TEA or DIPEA, in an organic solvent, e.g. NMP;

or c) converting a compound of formula I wherein $R^1$ is OH into a compound of formula I wherein $R^1$ is OPO$_3$H$_2$ or OCOR$^5$, $R^5$ being the residue of a naturally occurring amino acid, of the enantiomer of a naturally occurring amino acid or of dimethylaminoglycine;

or d) converting a compound of formula I$_{PG}$,

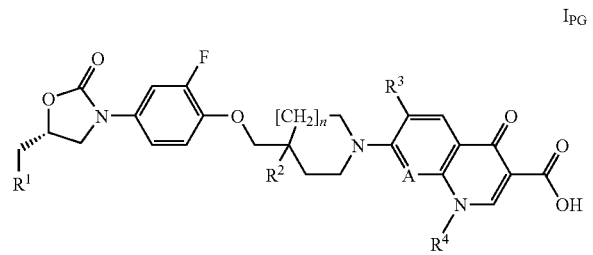

wherein $R^1$ is OPG$^1$ (PG$^1$ being a protecting group for an alcohol function), $R^2$ is OH, and n, $R^3$, $R^4$ and A have the same meaning as in formula I, into a compound of formula I wherein $R^2$ is OPO$_3$H$_2$ and subsequently removing the protecting group PG$^1$, examples of suitable protecting groups PG$^1$ being alkylsilyl or diarylalkylsilyl groups such as trimethylsilylt, tert-butyldimethylsilyl or tert-butyldiphenylsilyl (strategies to introduce these protecting groups and to remove them have been summarized in Protecting groups, Kocienski, P. J., *Thieme* (1994));

or e) converting a compound of formula VI

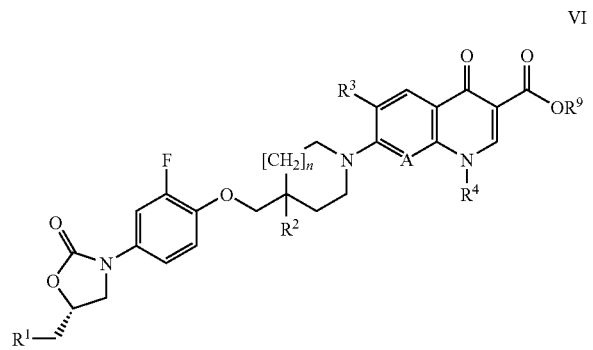

wherein $R^9$ is (C₁-C₅)alkyl (e.g. methyl, ethyl, n-propyl, iso-propyl or tert-butyl), aryl-(C₁-C₅)alkyl (e.g. benzyl, p-nitrobenzyl or p-methoxybenzyl), allyl, tri-(C₁-C₅) alkylsilyl (e.g. trimethylsilyl or tert-butyldimethylsilyl) or diaryl-(C₁-C₅)alkylsilyl (e.g. tert-butyldiphenylsilyl) and n, A, $R^1$, $R^2$, $R^3$ and $R^4$ are as defined in formula I into the corresponding compound of formula I by hydrolysis, saponification or hydrogenolysis (e.g. as reviewed in Protecting groups, Kocienski, P. J., *Thieme* (1994)).

Concerning the above process, the following should be noted:

❖ regarding variant a), the compound of formula III could also be replaced by an ester thereof, i.e. a compound of formula III$_E$

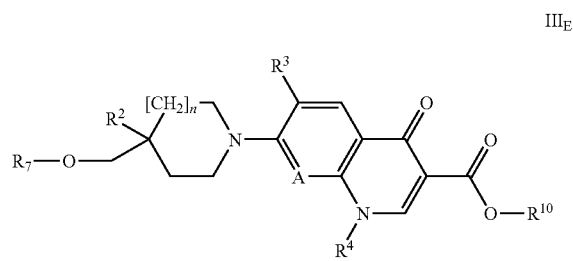

wherein n, A, $R^2$, $R^3$, $R^4$ and $R^7$ are as defined in formula III and R$^{10}$ represents alkyl, allyl or arylalkyl, in which case an ester deprotection step would follow the reaction of the compound of formula III$_E$ with the compound of formula II (general methods to perform the ester deprotection step have been reviewed in Protecting groups, Kocienski, P. J., Thieme (1994));

❖ regarding variant a), the compound of formula II could also be replaced by a silyl ether thereof i.e. a compound of formula II$_{PG}$

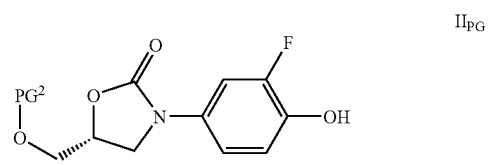

wherein PG$^2$ represents a silyl protecting group for an alcohol function such as a tri-(C₁-C₅)alkylsilyl (e.g. trimethylsilyl or tert-butyldimethylsilyi) or diaryl-(C₁-C₈) alkylsilyl (e.g. tert-butyldiphenylsilyl), in which case a deprotection step would follow the reaction of the compound of formula III or III$_E$ with the compound of formula II$_{PG}$ (general methods to perform such reactions have been reviewed in Protecting groups, Kocienski, P. J., Thieme (1994)), it being understood that when $R^2$ is H, the coupling between compound of formula II$_{PG}$ and the compound of formula III or III$_E$ can also be performed under Mitsunobu conditions as described in Synthesis (1981), 1, 1-28, and notably conditions wherein the reaction is carried out in the presence of DIAD and PPh$_3$;

❖ regarding variant b), the compound of formula IV could also be replaced by a compound of formula IV$_p$

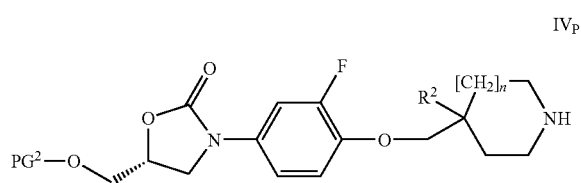

wherein n and $R^2$ are as defined in formula IV and PG$^2$ represents a protecting group for an alcohol function (e.g. an alkylsilyl or diarylalkylsilyl group such as trimethylsilyl, tert-butyldimethylsilyl or tert-butyldiphenylsilyl), in which case the appropriate deprotection step would follow the reaction of the compound of formula IV$_P$ with the compound of formula V (general methods to perform such reactions have been reviewed in Protecting groups, Kocienski, P. J., Thieme (1994));
* regarding variant b), when R$^8$ is not H, an additional ester deprotection step is required (general methods to perform such reactions have been reviewed in Protecting groups, Kocienski, P. J., Thieme (1994)), except for the cases wherein R$^8$ is BF$_2$ or B(OC(=O)(C$_1$-C$_4$)alkyl)$_2$ where the hydrolysis takes place already during the acidic work-up;
* regarding variant c), the compound of formula I wherein R$^1$ is OH can be replaced by a compound of formula VI wherein R$^1$ is OH and R$^2$ is H or OH, in which case an additional ester deprotection step is required (general methods to perform such reactions have been reviewed in Protecting groups, Kocienski, P. J., Thieme (1994));
* concerning variants c) and d):
    compounds of formula I wherein R$^1$ or R$^2$ is OPO$_3$H$_2$ can be obtained by deprotection of the corresponding compounds wherein R$^1$ or R$^2$ is OPO(OR)$_2$ and R is allyl or benzyl (according to the nature of R, various methods for deprotection may be used as reviewed in Protecting Groups, Kocienski, P., J., Thieme (1994), like for example catalytic hydrogenation over a noble catalyst such as palladium or hydrolysis with hydrobromic acid in a solvent such as AcOH when R is benzyl);
    compounds of formula I wherein R$^1$ is OCOR$^5$ can be obtained for example by reaction of compounds of formula I wherein R$^1$ is OH or compounds of formula VI wherein R$^1$ is OH and R$^2$ is H or OH with dimethylaminoglycine or a N-protected amino acid followed by deprotection of the amino group under standard conditions known to one skilled in the art (an additional ester deprotection step being required in the case of a reaction with a compound of formula VI).

The compounds of formula I obtained according to the abovementioned general preparation methods may then, if desired, be converted into their salts, and notably into their pharmaceutically acceptable salts.

Besides, whenever the compounds of formula I are obtained in the form of mixtures of enantiomers, the enantiomers can be separated using methods known to one skilled in the art (e.g. by formation and separation of diastereomeric salts or by chromatography over a chiral stationary phase). Whenever the compounds of formula I are obtained in the form of mixtures of diasteromers they may be separated by an appropriate combination of silica gel chromatography, HPLC and crystallization techniques.

Preparation of the Various Synthesis Intermediates:
Preparation of the Compound of Formula II The compound of formula II can be obtained by hydrogenation of compound VII

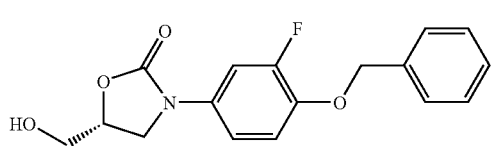

over a noble catalyst such as palladium or platinum on charcoal in a solvent such as THF, MeOH or AcOEt between 0° C. and 40° C. or by hydrolysis of in presence of a solution of HBr in water or AcOH between 0° C. and 80° C. in a solvent such as AcOH.

Preparation of the Compounds of Formula III

The compounds of formula III can be prepared as summarized in Scheme 1 hereafter.

Scheme 1

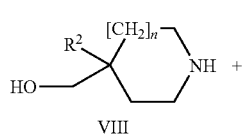

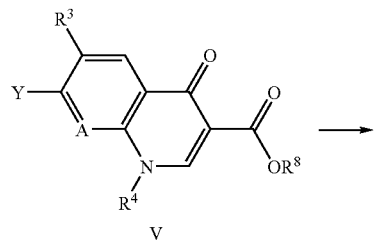

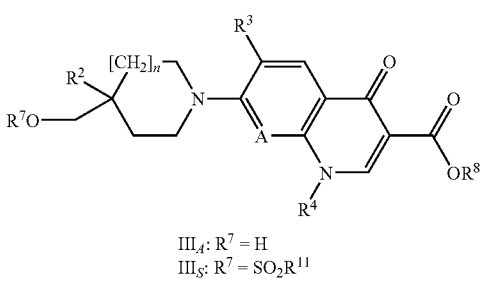

III$_A$: R$^7$ = H
III$_S$: R$^7$ = SO$_2$R$^{11}$

In Scheme 1, R$^8$ is H, alkyl, allyl or arylalkyl, and the other symbols are as before.

Compounds of formula III$_S$ wherein R$^2$ is H or OH, R$^7$ is SO$_2$R$^{11}$, R$^{11}$ being alkyl, trifluoromethyl or aryl like phenyl or p-tolyl are obtained (Scheme 1) from compounds of formula III$_A$ wherein R$^7$ is H by reaction with the corresponding sulfonyl chlorides in presence of an organic base such as TEA in a solvent such as DCM or THF between −10° C. and 50° C. Compounds of formula III$_A$ are prepared by reaction of the compounds of formula V with the piperidines of formula VIII in the presence of an organic base such as TEA or DIPEA between 40° C. and 100° C. in a solvent such as THF, DMF or NMP. If R$^8$ is benzyl, the carboxylic acid of formula III$_S$ is liberated according to standard procedures as described in Protecting groups, Kocienski, P. J., Thieme (1994) (e.g. hydrogenation over Pd/C).

The compounds of formula III wherein R$^2$ and R$^7$ together form a bond, i.e. the compounds of formula III$_O$

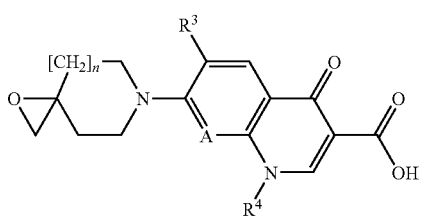

can be prepared by intramolecular cyclisation of the compounds of formula $III_S$ wherein $R^2$ is OH in the presence of an organic base (e.g. TEA) or an inorganic base (e.g. $K_2CO_3$ or an alkali methylate such as NaOMe or an alkali hydride such as NaH).

Preparation of the Compounds of Formula IV

The compounds of formula IV can be prepared as summarized in Scheme 2 hereafter.

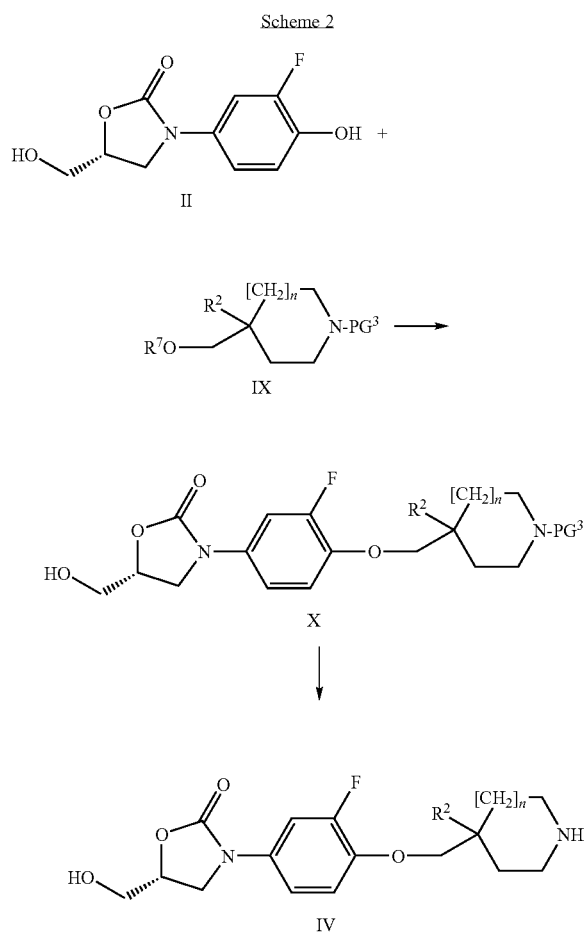

The compounds of formula I can be obtained by deprotecting a compound of formula X wherein $PG^3$ represents a nitrogen protecting group such as alkoxycarbonyl (e.g. Boc), benzyloxycarbonyl (e.g. Cbz), Alloc or benzyl. General methods to perform such protection/deprotection sequences of secondary nitrogen atoms have been reviewed in Protecting groups, Kocienski, P. J., Thieme (1994).

The compounds of formula X wherein $R^2$ is OH are obtained by reacting a compound of formula II with a compound of formula IX wherein either $R^2$ is OH and $R^7$ is $SO_2R^{11}$, $R^{11}$ being alkyl, trifluoromethyl or aryl like phenyl or p-tolyl, or $R^2$ and $R^7$ together form a bond (epoxide). Said epoxide can be obtained from compounds of formula IX, wherein $R^2$ is OH and $R^7$ is $SO_2R^{11}$ upon treatment with either an organic base such as TEA, pyridine or DBU or an inorganic base such as $K_2CO_3$ in a solvent such as THF, ether or DCM between −10° C. and 40° C. Compounds of formula X, wherein $R^2$ is H are obtained by reacting a compound of formula II with a compound of formula IX wherein $R^7$ is $SO_2R^{11}$. Compounds of formula IX are either commercially available (e.g. compounds of formula IX wherein $PG^3$ Boc, n=0 and $R^2$ and $R^7$ form an epoxide or wherein $PG^3$=Boc, n=1 and $R^2$=$R^7$=OH) or made as explained later on. Alternatively, compounds of formula X can be obtained by reaction of the compound of formula II with compounds of formula E wherein $R^7$ is H under Mitsunobu conditions.

Preparation of the Compounds of Formula V

Compounds of formula V wherein $R^8$ is H and Y halogen are commercially available (e.g. compounds wherein $R^3$=F, $R^4$=cyclopropyl and A=CH, CF or COMe, or $R^3$=F, $R^4$=Et and A=CH or CF, or $R^3$=F, $R^4$=cyclopropyl and A=N). Compounds of formula V wherein $R^8$ is $BF_2$ or $B(OC(=O)(C_1$-$C_4)alkyl)_2$ are obtained from compounds of formula V wherein $R^8$ is H according to WO 88/07998.

Preparation of the Compounds of Formula VI

The compounds of formula VI can be obtained by coupling compounds of formula IV or, alternatively, compounds of formula $IV_P$ as previously defined with compounds of formula V as previously defined except that $R^8$ represents ($C_1$-$C_5$)alkyl (e.g. methyl, ethyl, n-propyl, iso-propyl or tert-butyl), aryl-($C_1$-$C_8$)alkyl (e.g. benzyl, p-nitrobenzyl or p-methoxybenzyl), allyl, tri-($C_1$-$C_5$)alkylsilyl (e.g. trimethylsilyl or tert-butyldimethylsilyl) or diaryl-($C_1$-$C_5$)alkylsilyl (e.g. tert-butyldiphenylsilyl), under the same conditions as those described for the reaction of the compounds of formula IV with the compounds of formula V. If the compounds of formula $IV_P$ are used, the deprotection step can be carried out after the coupling reaction.

Preparation of the Compound of Formula VII

The compound of formula VII can be obtained according to WO 2004/096221.

Preparation of the Compounds of Formula VIII

Compounds of formula VIII are either commercially available ($R^2$H) or obtained by deprotection of compounds of formula IX ($R^2$=OH and $R^7$=H), for example by treatment of the corresponding Boc protected compounds with TFA or by hydrogenation of the corresponding Cbz protected compounds over Pd/C.

Preparation of the Compounds of Formula IX

The compounds of formula IX can be prepared from the methylidene derivatives of formula XI as summarized in Scheme 3 hereafter.

Scheme 3

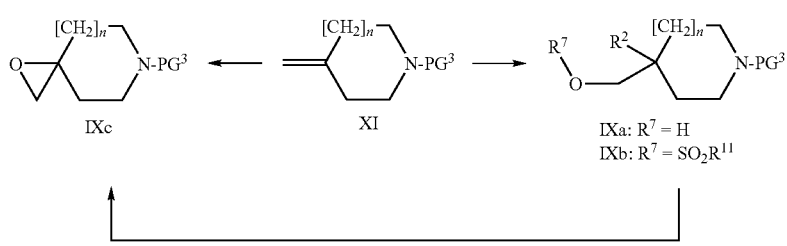

The compounds of formula IXb, i.e. the compounds of formula IX wherein $R^2$ is H or OH and $R^7$ is $SO_2R^{11}$, are prepared from the corresponding compounds of formula IXa wherein $R^7$ is H using the same methods used for the conversion of compounds of formula $III_A$ into compounds of formula $III_S$. Compounds of formula a either are commercially available ($R^2$=H) or are obtained from the known methylidene derivatives of formula XI (e.g. those wherein n=0 and $PG^3$=benzyl, Boc or benzyloxycarbonyl—see EP 241206 and EP 550025; or those wherein n=1 and $PG^3$=benzyl, Boc which are commercial) either by osmium tetroxide catalyzed cis-dihydroxylation or by its asymmetric version (Sharpless dihydroxylation using AD-mix α or β) as described in *J. Am. Chem. Soc.* (1988), 110, 1968 ($R^2$=OH). Compounds of formula IXc, i.e. the compounds of formula IX wherein $R^2$ and $R^7$ together form a bond (epoxide), are obtained either by intramolecular ring closure of compounds of formula IXb with an inorganic base such as $K_2CO_3$ or NaH or an organic base such as TEA or DBU, or by epoxidation of the methylidene double bond with a peracid such as MCPBA. Alternatively, compounds of formula IXc can also be obtained by reaction of the corresponding oxo derivatives (commercial when n 0 or 1 and $PG^3$=Cbz or Boc) with trimethylsulfoxonium iodide or trimethylsulfonium iodide in presence of an alkali hydroxide such as KOH in a polar solvent such as MeCN between 20 and 100° C. (as described in *J. Am. Chem. Soc.* (1965), 87, 1353-1364 and *Tetrahedron Lett.* (1987), 28, 1877-1878).

The following examples further illustrate the preparation of the pharmacologically active compounds of the invention but do not limit the scope thereof.

EXAMPLES

All temperatures are stated in ° C. All analytical and preparative HPLC investigations on non-chiral phases are performed using RP-C18 based columns. Analytical HPLC investigations are performed on two different instruments with cycle-times of ~2.5 min and ~3.5 min respectively. Unless otherwise stated, the values indicated for MS correspond to the main peaks ((M+H)$^+$ with a variation of +/−0.5 unit). In NMR spectra, coupling constants J are given in Hz.

Standard Work-Up Procedure:

After dilution in the appropriate org. solvent (see corresponding Example text), the org. phase is separated and sequentially washed with water and brine. In case of reaction performed in a water soluble solvent (e.g. MeOH, THF or DMF), the combined aq. layers are back-washed with the same solvent used to perform the workup. The combined org. phases are dried over $MgSO_4$ and filtered, The filtrate is evaporated under reduced pressure.

Standard Chromatography Procedure:

The crude material is dissolved in the minimum of eluent (see corresponding Example text) and chromatographed over $SiO_2$. The relevant fractions were pooled and evaporated under reduced pressure.

Example 1

1-cyclopropyl-6-fluoro-7-{4-[2-fluoro-4-((R)-5-hydroxymethyl-2-oxo-oxazolidin-3-yl)-phenoxymethyl]-4-hydroxy-piperidin-1-yl}-4-oxo-1,4-dihydro-quinoline-3-carboxylic acid 1.i (R)-3-(3-fluoro-4-hydroxy-phenyl)-5-hydroxymethyl-oxazolidin-2-one A solution of (R)-3-(4-benzyloxy-3-fluoro-phenyl)-5-hydroxymethyl-oxazolidin-2-one (6.34 g, prepared according to WO 2004/096221) in THF/MeOH (1:1; 200 mL) was hydrogenated over Pd/C 10% (1 g) overnight. The catalyst was filtered off, the filtrate evaporated under reduced pressure and the residue stirred in EA. The crystals were collected by filtration, affording 3.16 g (70% yield) of a colorless solid.

$^1$H NMR (DMSO$_{d6}$; δ ppm): 3.5 (m, 1H), 3.64 (m, 1H), 3.74 (dd, J=8.8, 6.4, 1H), 3.99 (t, J=8.8, 1H), 4.64 (m, 1H), 5.16 (t, J=5.6, 1H), 6.93 (dd, J=9.7, 8.8, 1H), 7.08 (ddd, J=8.8, 2.6, 1.2, 1H), 7.45 (dd, J=13.5, 2.6, 1H), 9.66 (s, 1H).

MS (ESI): 228.1.

1.ii. 4-[2-fluoro-4-((R)-5-hydroxymethyl-2-oxo-oxazolidin-3-yl)-phenoxymethyl]-4-hydroxy-piperidine-1-carboxylic acid benzyl ester A solution of intermediate 1.i (1.27 g) and 1-oxa-6-azaspiro[2.5]octane-6-carboxylic acid benzyl ester (1.60 g; prepared according to U.S. Pat. No. 4,244,961) were dissolved in DMF (15 mL) and treated with $Na_2CO_3$ (1.16 g). The mixture was heated at 100° C. overnight. The residue obtained after workup (DCM) was stirred in EA, and the solid was collected by filtration and sequentially washed with EA and Hex, affording 2.52 g (94.5% yield) of a beige solid.

$^1$H NMR (DMSO$_{d6}$; δ ppm): 1.57 (m, 4H), 3.14 (m, 2H), 3.54 (m, 1H), 3.64 (m, 1H), 3.79 (m, 5H), 4.03 (t, J=9.1, 1H), 4.66 (m, 1H), 4.78 (s, 1H), 5.05 (s, 2H), 5.16 (t, J=5.6, 1H), 7.18 (m, 2H), 7.32 (m, 5H), 7.55 (d, J=12, 1H).

MS (ESI): 475.0.

1.iii. (R)-3-[fluoro-4-(4-hydroxy-piperidin-4-yl-methoxy)-phenyl]-5-hydroxymethyl-oxazolidin-2-one A suspension of intermediate 1.ii (2.5 g) in EA/MeOH (1:1; 100 mL) was hydrogenated over Pd/C for 48 h. The suspension was heated at 40° C. and the catalyst was filtered off. The filtrate was evaporated under reduced pressure affording 1.61 g (89% yield) of a yellow powder.

$^1$H NMR (DMSO$_{d6}$; δ ppm): 1.4-1.63 (m, 4H), 2.67 (m, 2H), 2.83 (m, 2H), 3.53 (dd, J=4.0 and 12.0, 1H); 3.66 (dd, J=3.3 and 12.0, 1H), 3.71 (s, 2H); 3.80 (m, 1H), 4.05 (t, J=9.0, 1H), 4.48 (s, 1H), 4.68 (m, 1H), 5.20 (s, 1H), 7.20 (m, 2H), 7.57 (d, 1H).

MS (ESI): 341.5.

1.iv. 1-cyclopropyl-6-fluoro-7-[4-[2-fluoro-4-((R)-5-hydroxymethyl-2-oxo-oxazolidin-3-yl)-phenoxymethyl]-4-hydroxy-piperidin-1-yl]-4-oxo-1,4-dihydro-quiinoline-3-carboxylic acid A solution of intermediate 1.iii (200 mg), 7-chloro-1-cyclopropyl-6-fluoro-1,4-dihydro-4-oxo-3-quinolinecarboxylic acid boron diacetate complex (241 mg; prepared according to WO 88/07998) and DIPEA (100 µl) in NMP (2 mL) was stirred at 85° C. for 5 h. The reaction mixture was evaporated under reduced pressure and the residue was taken up in 5M HCl in MeOH (3 mL) and stirred. The resulting solid was collected by filtration and washed with MeOH to afford 230 mg (67% yield) of a yellow solid.

$^1$H NMR (DMSO$_{d6}$; δ ppm): 1.66-1.35 (m, 4H), 1.75 (d, J 12.8, 2H), 1.95 (m, 2H), 3.33 (t broad, J=11.0, 2H), 3.57 (m, 3H), 3.67 (dd, J=12.3, 3.3, 1H), 3.83 (m, 2H), 3.92 (s, 2H), 4.06 (t, J=9.0, 1H), 4.69 (m, 1H), 7.24 (m, 2H), 7.60 (m, 2H), 7.90 (d, J=13.3, 1H), 8.66 (s, 1H).

MS (ESI): 585.9.

Example 2

1-cyclopropyl-6-fluoro-7-{4-[2-fluoro-4-((R)-5-hydroxymethyl-2-oxo-oxazolidin-3-yl)-phenoxymethyl]-piperidin-1-yl}-4-oxo-1,4-dihydro-quinoline-3-carboxylic acid 2.i. (R)-3-(4-benzyloxy-3-fluoro-phenyl)-5-(tert-butyl-dimethyl-silanyloxymethyl)-oxazolidin-2-one A solution of TBDMSCl (3.77 g) in DCM (5 mL) was added dropwise at 0° C. to a solution of (R)-3-(4-benzyloxy-3-fluoro-phenyl)-5-hydroxymethyl-oxazolidin-2-one (6.35 g; prepared according to WO 2004/096221) and imidazole (2.04 g) in DMF (15 mL). After stirring at rt for 16 h, the reaction mixture concentrated in vacuo. The residue was taken up in DCM and sequentially washed with 1N HCl, sat. Na CO$_3$ aq. and brine, dried over MgSO$_4$, filtered and concentrated to give 8.41 g (97% yield) of a colorless solid.

$^1$H NMR (DMSO$_{d6}$; δ ppm): 0.04 (6H, s); 0.79 (9H, s); 3.69-3.78 (2H, m), 3.86 (1H, dd, J=3 and J=12); 4.07 (1H, t, J=9); 4.69-4.77 (1H, m); 5.15 (2H, s); 7.15-7.21 (1H, m); 7.25 (1H, t, J=9); 7.30-7.36 (1H, m); 7.37-7.50 (4H, m); 7.57 (1H, dd, J=3 and J=14).

2.ii. R)-5-(tert-butyl-dimethyl-silanyloxymethyl)-3-(3-fluoro-4-hydroxy-phenyl)-oxazolidin-2-one A solution of intermediate 2.i (7.22 g) in THF/MeOH (1:1; 150 mL) was hydrogenated over 10% Pd/C (150 mg) for 3 h. The catalyst was filtered off and the filtrate concentrated in vacuo affording 5.51 g (96% yield) of a colorless solid.

$^1$H NMR (DMSO$_{d6}$; δ ppm). 0.04 (6H, s); 0.80 (9H, s); 3.69-3.78 (2H, m), 3.86 (1H, dd, J=3 and J=12); 4.07 (1H, t, J=9); 4.68-4.75 (1H, m); 6.94 (1H, t, J=9); 7.04-7.10 (1H, m); 7.45 (1H, dd, J=3 and J=14); 9.65 (1H, s).

MS (ESI): 342.2.

2.iii. 4-[4-[(R)—S-(tert-butyl-dimethyl-silanyloxymethyl)-2-oxo-oxazolidin-3-yl]-2-fluoro-phenoxymethyl]-piperidine-1-carboxylic acid tert-butyl ester A suspension of 4-hydroxymethylpiperidine-1-carboxylic acid tert-butyl ester (200 mg; commercial), intermediate 2.ii (317 mg) and PPh$_3$ (365 mg) in THF (5 mL) was treated dropwise over 90 min with DIAD (0.294 mL). After stirring overnight at rt, the reaction mixture was worked up (toluene/Hex 1:2) and chromatographed (Hex/EA 2:1), affording 351 mg (70% yield) of an off-white solid.

MS (ESI): 539.2.

2.iv. (R)-3-[3-fluoro-4-(piperidin-4-ylmethoxy)-phenyl]-5-hydroxymethyl-oxazolidin-2-one A solution of intermediate 2.iii (351 mg) in MeOH (2 mL) was treated with 5M HCl in MeOH (1 mL) and stirred at rt for 3 h. The resulting solid was collected by filtration and washed with MeOH (5 mL), affording 180 mg (85% yield) of a colorless solid.

$^1$H NMR (DMSO$_{d6}$; δ ppm): 1.48 (2H, m); 1.89 (2H, m); 2.05 (1H, m); 2.88 (2H, t, J=10); 3.10 (2H, m); 3.55 (1H, m); 3.63 (1H, m); 3.78 (1H, dd, J=6.4 and J=8.8); 3.91 (2H, d, J=6.2); 4.02 (1H, t, J=8.8); 4.66 (1H, m); 5.19 (1H, t, J=5.6); 7.20 (2H, m); 7.56 (1H, dd, J=2.35 and J=14).

MS (ESI): 325.5.

2.v. 1-cyclopropyl-6-fluoro-7-{4-[2-fluoro-4-((R)-5-hydroxymethyl-2-oxo-oxazolidin-3-yl)-phenoxymethyl]-piperidin-1-yl}-4-oxo-1,4-dihydro-quinoline-3 carboxylic acid The title compound was obtained as a colorless powder in 12% yield, starting from intermediate 2.iv (177 mg) and 7-chloro-1-cyclopropyl-6-fluoro-1,4-dihydro-4-oxo-3-quinolinecarboxylic acid boron diacetate complex (205 mg) and following the procedure of Example 1, step 1.iv.

$^1$H NMR (DMSO$_{d6}$; δ ppm): 113-1.33 (m, 4H), 1.45-1.6 (m, 2H), 1.94 (dl, J=12.0, 2H), 2.04 (m, 1H), 2.98 (t, J=12.0, 2H), 3.50-3.69 (m, 2H), 3.73-3.89 (m, 4H), 3.98 (d, J=6.2, 2H), 4.02 (t, J=9.3, 1H), 4.66 (m, 1H), 5.18 (t, J=5.6, 1H), 7.21 (m, 2H), 7.56 (m, 2H), 7.88 (d, J=13.5, 1H), 8.64 (s, 1H).

MS (ESI): 570.2.

Example 3

1-cyclopropyl-6-fluoro-7-[4-[2-fluoro-4-((R)-5-hydroxymethyl-2-oxo-oxazolidin-3-yl)-phenoxymethyl]-4-hydroxy-piperidin-1-yl]-4-oxo-1,4-dihydro-[1,8]naphthyridine-3-carboxylic acid A solution of 7-chloro-1-cyclopropyl-6-fluoro-1,4-dihydro-4-oxo-1,8-naphthyridine-3-carboxylic acid (166 mg; commercial) and intermediate 1.iii (200 mg) in NMP (5 mL) was treated with TEA (0.32 mL) and TMSCl and heated at 85° C. for 5 h. The reaction mixture was evaporated under reduced pressure and the residue was taken up in 5M HCl in MeOH (3 mL) and stirred for 30 min. The solution was evaporated under reduced pressure and the residue was taken up in EA. The resulting solid was collected by filtration and washed with EA, affording 271 mg (78% yield) of a yellow solid.

$^1$H NMR (DMSO$_{d6}$; δ ppm): 0.89-1.27 (4H, m); 1.78 (2H, d, J=12.8); 1.90-2.04 (2H, m); 3.53-3.88 (6H, m); 3.88 (2H, s), 4.06 (1H, t, J=9.0), 4.42 (2H, d broad, J=13.2), 4.44 (1H, m); 7.11 (2H, m); 7.55 (1H, d, J=14.5); 8.05 (1H, d, J=13.5); 8.60 (1H, s).

MS (ESI): 586.8.

Example 4

7-(4-{-4-[(R)-5-((S)-2-amino-propionyloxymethyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid hydrochloride

4.i. 1-cyclopropyl-6-fluoro-7-[4-[2-fluoro-4-((R)-5-hydroxymethyl-2-oxo-oxazolidin-3-yl)-phenoxymethyl]-4-hydroxy-piperidin-1-yl]-4-oxo-1,4-dihydro-quinoline-3-carboxylic acid benzyl ester A suspension of intermediate 1.iv (300 mg) and $K_2CO_3$ (77.8 mg) in DMF (10 mL) was treated with BnBr (82 tl) and stirred at 80° C. for 2 days. The solvents were removed under reduced pressure. The residue was worked up (DCM) and purified by chromatography (DCM/IeOH 95:5) affording 219 mg (63% yield) of a white powder.

$^1$H NMR (DMSO$_{d6}$; δ ppm): 1.0-1.25 (4H, m); 1.71 (2H, dd, J=0.6 and J=12.9); 1.92 (2H, m); 3.25 (2H, m); 3.50 (3H, m); 3.65 (2H, m); 3.78 (1H, dd, J=6.4 and J=8.8); 3.89 (2H, s); 4.03 (1H, t, J=9.1); 4.65 (In, m); 4.82 (1H, s); 5.17 (1H, t, J=5.6); 5.25 (2H, s); 7.21 (2H, m); 7.35-7.60 (7H, m); 7.74 (1H, d, J=13.5); 8.45 (1H, s).

MS (ESI): 676.2.

4.ii. 7-(4-{4-[(R)-5-((S)-2-tert-butoxycarbonylamino-propionyloxymethyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid benzyl ester A solution of intermediate 4.i (219 mg) in DMF (3 mL) was treated with Boc-L-Ala-OH (79.7 mg), EDC (81 mg) and DMAP (20 mg). The reaction was stirred at rt for 2 h. The DMF was evaporated under reduced pressure and the residue was purified by chromatography (DCM/MeOH 95:5). The relevant fractions were evaporated under reduced pressure and stirred in ether. The solid was collected by filtration affording 280 mg (100% yield) of a white foam.

$^1$H NMR (DMSO$_{d6}$; δ ppm): 1.06-11.11 (2H, m); 1.17-1.27 (5H, m); 1.34 (9H, s); 1.67-1.76 (2H, d, J=12); 1.86-1.99 (2H, m); 3.18-3.25 (2H, m); 3.40-3.50 (2H, m); 3.60-3.72 (1H, m); 3.77-3.85 (1H, m); 3.89 (2H, s); 3.96-4.04 (1H, t, J=7.3); 4.10 (111, t, J=9); 4.2-43 (1H, dd, J=4.7 and J=13.2); 4.38-4.44 (1H, d, J=11.7); 4.83-4.95 (1H, m); 5.26 (2H, s); 7.20-7.55 (9H, m); 7.75 (1H, d, J=12.6); 8.46 (1H, s).

MS (ESI): 847.5.

4.iii. 7-(4-{4-[(R)-5-((S-2-tert-butoxycarbonylamino-propionyloxymethyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid A solution of intermediate 4.ii (285.3 mg) in dioxane/MeOH (1:1; 10 mL) was hydrogenated over 10% Pd/C (10 mg) for 4 h. The catalyst was removed by filtration and washed with MeOH (2 mL). The filtrate was evaporated under reduced pressure affording 215 mg (84.4% yield) of yellow foam,

MS (ESI): 757.3.

4.iv. 7-(4-{4-[(R)-5-((S)-2-amino-propionyloxymethyl)-2-oxo-oxazolidin-3 yl]-2-fluoro-phenoxymethyl}-4-hydroxy-piperidin-1-yl)-1-cyclopropyl-6-fluoro-4 oxo-1,4-dihydro-quinoline-3-carbocylic acid hydrochloride A solution of intermediate 4.iii (193 mg) in dioxane (1 mL) was treated with 0.15 mL HCl (5M in dioxane). The reaction was stirred at rt for 14 h. The solvent was evaporated under reduced pressure. The residue was taken up in dioxane (10 mL) and the resulting solid was collected by filtration affording 153 mg (86.7% yield) of a yellow powder. $^1$H NMR (DMSO$_{d6}$; δ ppm): 1.15-1.33 (4H, m); 1.35 (3H, d, J=6.4); 1.73 (2H, d, J=13); 1.93 (2H, m); 3.31 (2H, t, J=11); 3.84 (4H, m); 4.13 (2H, m); 4.35 (1H, dd, J=5 and J=12); 4.55 (2H, dd, J=2 and J=12); 4.95 (1H, m); 7.23 (2H, m); 7.56 (2H, m); 7.88 (1H, d, J=13.2); 8.51 (211, si); 8.64 (1H, s).

MS (ESI): 657.3.

Example 5

1-cyclopropyl-6-fluoro-7-{4-[2-fluoro-4-((R)-2-oxo-5-phosphonooxymethyl-oxazolidin-3-yl)-phenoxymethyl]-4-hydroxy-piperidin-1-yl}-4-oxo-1,4-dihydro-quinoline-3-carboxylic acid

5.i. 7-(4-{4-[(R)-5-(bis-benzyloxy-phosphoryloxymethyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid A suspension of intermediate 1.iv (300 mg) and 4,5-dicyanoimidazole (109 mg) in DCM (3 mL) was treated at 0° C. with dibenzyl N,N-diisopropylphosphoramidite (0.303 mL). The reaction was stirred at rt for 1 h. A 70% tert-butyl hydroperoxide solution in water (0.147 mL) was added. The solution was stirred 1 h at RT. The solvent was evaporated under reduced pressure and the residue was worked up (DCM) and purified by chromatography (DCM/MeOH 95:5), affording 214 mg (49.45% yield) of an off-white foam.

MS (ESI): 846.3.

5.ii. 1-cyclopropyl-6-fluoro-7-{4-[2-fluoro-4-((R)-2-oxo-5-phosphlonooxymethyl-oxazolidin-3-yl)-phenoxymethyl]-4-hydroxy-piperidin-1-yl}-4-oxo-1,4-dihydro-quinoline-3-carboxylic acid A solution of intermediate 5.i (214 mg) in AcOH (1.5 mL) was treated with HBr (1.5 mL; 33% in AcOH). The reaction mixture was stirred at RT for 2 h and poured into water (20 mL). The gum was stirred for 1 h and decanted. The oily material was taken up in EA (20 mL) and further stirred for 2 h. The solid was collected by filtration and further stirred in DCM (10 mL). The solid was collected by filtration, affording 110 mg (65% yield) of a yellow powder.

$^1$H NMR (DMSO$_{d6}$; δ ppm): 1.18-1.30 (4H, m); 1.73 (1H, d, J=13); 1.95 (2H, m); 2.40 (2H, d, J 13); 3.26 (2H, m); 3.58

(2H, m); 3.76-3.87 (2H, m); 3.90 (1H, s); 3.95-4.15 (3H, m); 4.47 (1H, s); 4.86 (1H, m); 7.21 (2H, m); 7.57 (2H, m); 7.89 (1H, dd, J=5.9 and J=13.2); 8.65 (1H, s).
MS (ESI): 666.2.

Example 6

1-cyclopropyl-6-fluoro-7-{(RS)-3-[2-fluoro-4-((R)-5-hydroxymethyl-2-oxo-oxazolidin-3-yl)-phenoxymethyl]-3-hydroxy-pyrrolidin-1-yl}-4-oxo-1,4-dihydro-quinoline-3-carboxylic acid 6.i. Diallyl-carbamic acid benzyl ester Benzoyl chloride (15.5 mL) was added dropwise over 30 min to a solution of diallylamine (12.3 mL) and TEA (21 mL) in DCM (100 mL) at 0° C. The reaction mixture was stirred at rt for 16 h. The residue obtained after work up (DCM) was purified by chromatography (Hex/EA 95:5) to give 20.71 g (88% yield) of a colorless liquid.
$^1$H NMR (DMSO$_{d6}$; δ ppm): 3.83 (4H, dt, J=1 and J=6); 5.05-5.18 (6H, m); 5.70-5.86 (2H, m); 7.27-7.48 (5H, m).

6.ii. 2,5-dihydro-pyrrole-1-carboxylic acid benzyl ester

Benzylidene-bis(tricyclohexylphosphine)dichlororuthenitsm (5 g) was added to a solution of intermediate 6.i (17.56 g) in DCM (1.5 l) at rt under nitrogen. The reaction mixture was stirred at 40° C. for 2 h and concentrated in vacuo. The residue was purified by chromatography (Hex/EA 90:10) to give 14.08 g (91% yield) of a yellow liquid.
$^1$H NMR (DMSO$_{d6}$; δ ppm): 4.05-4.16 (4H, m); 5.08 (2H, s); 5.81-5.92 (2H, m); 7.27-7.41 (5H, m).

6.iii. (RS)-3-hydroxy-pyrrolidine-1-carboxylic acid benzyl ester

A 1M solution of borane in THF (9 mL) was added to a solution of intermediate 6.ii (1.81 g) in THF (25 mL) at 0° C. under nitrogen. The reaction mixture was stirred at rt for 16 k and was cooled to 0° C. 20% NaOH (1.8 mL) was carefully added dropwise followed by 35% aq. hydrogen peroxide (1.2 mL). The mixture was stirred at 0° C. for 30 min and at rt for 2 h. Et$_2$O and an aq. 40% sodium bisulfite solution were added and the reaction mixture stirred vigorously for 15 min. The residue obtained after work up (Et$_2$O) was purified by chromatography (Hex/EA 5:5 to 3:7) to give 1.01 g (51% yield) of a colorless oil.
$^1$H NMR (DMSO$_{d6}$; δ ppm): 1.67-1.82 (1H, m); 1.82-1.96 (1H, m); 3.16-3.25 (1H, m); 3.28-3.44 (3H, m); 4.20-4.29 (1H, broad); 4.92 (1H, d, J=3); 5.06 (2H, s); 7.27-7.41 (5H, m).

6.iv. 3-oxo-pyrrolidine-1-carboxylic acid benzyl ester

A solution of intermediate 6.iii (1.10 g) in DCM (8 mL) was cooled to 0° C. and DIPEA (2.5 mL) was added dropwise, followed by a solution of sulfur trioxide pyridine complex (1.79 g) in DMSO (6.5 mL). The reaction mixture was stirred at 0° C. for 1 h and was quenched by the addition of water (6 mL). The aq. layer was extracted with Et$_2$O/Hex (1:1, 3×5 mL) and the combined org. layers were concentrated in vacuo. The residue obtained after work up (Et$_2$O/Hex 1:1) was purified by chromatography (Hex/EA 5:5) to give 1.05 g (96% yield) of a yellowish oil.
$^1$H NMR (DMSO$_{d6}$; δ ppm): 2.48-2.61 (2H, m); 3.61-3.80 (4H, m); 5.09 (2H, s); 7.27-7.41 (5H, m).

6.v. 3-methylene-pyrrolidine-1-carboxylic acid benzyl ester t-BuOK (617 mg) was added in one portion to a white suspension of methyl triphenylphosphonium bromide (1.98 g) in THF (10 mL) at rt under nitrogen. The yellow suspension was stirred at rt for 1 h and then cooled to −10° C. A solution of intermediate 6.iv (1.05 g) in THF (2 mL) was added dropwise over 10 min and the reaction mixture was allowed to warm to rt over 2 h. The reaction was quenched by the addition of sat. aq. NH$_4$Cl (1 mL) and diluted with EA. The residue obtained after work up (EA) was purified by chromatography (Hex/EA 90:10) to give 633 mg (64% yield) of a yellowish liquid.
$^1$H NMR (DMSO$_{d6}$; δ ppm)-2.48-2.61 (2H, m); 3.36-3.53 (2H, m); 3.84-4.01 (2H, m); 4.97-5.03 (2H, m); 5.08 (2H, s); 7.27-7.41 (5H, m).

6.vi. 1-oxa-5-aza-spiro[2.4]heptane-5-carboxylic acid benzyl ester

A solution of intermediate 6.v (7.21 g) in DCM (400 mL) was treated with MCPBA (20.1 g) and NaHCO$_3$ (22.3 g) at rt. The reaction was stirred at rt for 2 h, diluted with DCM (200 mL) and poured in a solution of Na$_2$SO$_3$ (45 g) in water (400 mL). The mixture was stirred for 10 min and the org. layer was separated. The residue obtained after work up (DCM) was purified by chromatography (Hex/EA 6:4) to give 4.37 g (56% yield) of a yellow oil.
$^1$H NMR (DMSO$_{d6}$; δ ppm): 1.70-1.83 (1H, m); 2.22-2.37 (1H, m); 2.90-2.94 (1H, m); 2.95-2.99 (1H, m); 3.15 (1H, t, J=11); 3.39-3.77 (3H, m); 5.09 (2H, s); 7.27-7.41 (5H, m).

6.vii. (S)-3-[2-fluoro-4-((R)-5-hydroxymethyl-2-oxo-oxazolidin-3-yl)-phenoxymethyl]-3-hydroxy-pyrrolidine-1-carboxylic acid benzyl ester K$_2$CO$_3$ (274 mg) was added to a suspension of intermediate 1.i (300 mg) and intermediate 6.vi (338 mg) in DMF (3 mL). The reaction mixture was stirred at 80° C. for 3 h and the solvent was removed in vacuo. The residue obtained after work up (DCM) was purified by chromatography (DCM/MeOH 95:5) to give 531 mg (87% yield) of a beige foam.
$^1$H NMR (DMSO$_{d6}$; δ ppm): 1.80-1.92 (1H, m); 1.96-2.08 (1H, m); 3.32-3.59 (5H, m); 3.66 (1H, ddd, J=3, J=6 and J=13); 3.80 (1H, dd, J=6 and J=9); 3.97-4.09 (3H, m); 4.64-4.72 (1H, m); 5.07 (2H, s); 5.19 (1H, t, J 6); 5.23 (1H, s); 7.18-7.23 (2H, m); 7.27-7.38 (5H, m); 7.57 (1H, dd, J=2 and J=14).
MS (ESI): 460.9.

6.viii. (R)-3-[3-fluoro-4-((RS)-3-hydroxy-pyrrolidin-3-ylmethoxy)-phenyl]-5-hydroxymethyl-oxazolidin-2-one A solution of intermediate 6.vii (259 mg) in THF/MeOH (1:1; 20 mL) was hydrogenated over 10% Pd/C (60 mg) for 20 h at rt. The reaction mixture was concentrated in vacuo, taken in DCM/MeOH 90:130 (20 mL) and stirred at rt for 30 min. The catalyst was filtered off and the filtrate concentrated in vacuo to give 184 mg (100% yield) of an orange foam.
MS (ESI): 327.3.

6.ix. 1-cyclopropyl-6-fluoro-7-[(RS)-3-[2-fluoro-4-((R)-5-hydroxymethyl-2-oxo-oxazolidin-3-yl)-phenoxymethyl]-3-hydroxy-pyrrolidin-1-yl]-4-oxo-1,4 dihydro-quinoline-3-carboxylic acid A solution of intermediate 6.viii (226 mg) and 7-chloro-1-cyclopropyl-6-fluoro-1,4-dihydro-4-oxo-3-quinolinecarboxylic acid boron diacetate complex (270 mg; prepared according to WO 88/07998) in NMP (5 mL) was treated with DIPEA (120 μL) and stirred at 60° C. for 2 h. The reaction mixture was concentrated in vacuo and the residue was taken in 5M HCl in MeOH (2 mL). The solution was stirred at rt for 1 h, concentrated in vacuo and the residue was purified by chromatography (DCM/MeOH/AcOH 95.4:1 to 90:9:1). The foamy residue was taken in MeOH (2 mL), stirred for 1 h and filtered. The crystals were collected and dried in vacuo to afford 23 mg (6% yield) of a beige solid.

$^1$H NMR (DMSO$_{d6}$; δ ppm): 1.10-1.34 (4H, m); 1.98-2.10 (TH, m); 2.14-2.26 (TH, m); 3.48-3.70 (3H, m); 3.71-3.89 (5H, m); 4.05 (1H, t, J=9); 4.09-4.18 (2H, m); 4.66-4.74 (1H, m); 5.19 (1H, t, J=6); 5.40 (1H, s); 7.09 (1H, d, J=8); 7.18-7.31 (2H, m); 7.59 (1H, dd, J=2 and J=14); 7.82 (1H, d, J=14); 8.59 (1H, s); 15.52 (1H, s).

MS (ESI): 572.3.

Example 7

1-cyclopropyl-6-fluoro-7-{(RS)-3-[2-fluoro-4-((R)—S-hydroxymethyl-2-oxo-oxazolidin-3-yl)-phenoxymethyl]-3-hydroxy-pyrrolidin-1-yl}-8-methoxy-4-oxo-1,4-dihydro-quinoline-3-carboxylic acid This compound was obtained as a yellow solid in 52% yield, starting from intermediate 6.viii (85 mg), 1-cyclopropyl-6,7-difluoro-1,4-dihydro-8-methoxy-4-oxo-3-quinolinecarboxylic acid boron diacetate complex (100 mg; prepared according to Sakurai et al., *Bioorg. Med. Chem. Lett.* (1998), 8, 2185-2190) and DIPEA (43 μl) and following the procedure of Example 6, step 6.ix. The foamy residue was stirred in EA (5 mL) and dried.

MS (ESI): 602.2.

Example 8

1-cyclopropyl-6-fluoro-7-{(RS)-3-[2-fluoro-4-((R)-5-hydroxymethyl-2-oxo-oxazolidin-3-yl)-phenoxymethyl]-pyrrolidin-1-yl}-4-oxo-1,4-dihydro-quinoline-3-carboxylic acid 8.i. (RS)-3-hydroxymethyl-pyrrolidine-1-carboxylic acid benzyl ester This compound was obtained as a colorless oil in 68% yield, starting from intermediate 6.v (630 mg) and a 1M solution of borane in THEF (9 mL), and following the procedure of Example 6, step 6.iii.

$^1$H NMR (DMSO$_{d6}$; δ ppm): 1.51-1.71 (1H, m); 1.79-1.97 (1H, m); 2.19-2.35 (1H, m); 3.00-3.15 (1H, m); 3.19-3.50 (5H, m); 4.65 (1H, t, J=5); 5.05 (2H, s); 7.27-7.40 (5H, m).

MS (EST): 235.9.

8.ii (RS)-3-{4-[(R)-5-(tert-butyl-dimethyl-silanyloxymethyl)-2-oxo-oxazolidin-3-yl]-2-fluoro-phenoxymethyl}-pyrrolidine-1-carboxylic acid benzyl ester A suspension of intermediate 8.i (456 mg), intermediate 2.ii (630 mg) and PPh$_3$ (726 mg) in THF (8 mL) was treated dropwise over 2 h with DIAD (0.55 mL) at rt. The reaction mixture was further stirred at rt for 2 h and was concentrated in vacuo. The residue was purified by chromatography (Hex/EA 7:3 to 6:4) to give 966 mg (94% yield) of a yellow oil.

$^1$H NMR (DMSO$_{d6}$; δ ppm): 0.04 (6H, s); 0.79 (9H, s); 1.65-1.82 (1H, m); 1.93-2.08 (1H, m); 2.56-2.74 (1H, m); 3.14-3.25 (1H, m); 3.30-3.59 (3H, m); 3.69-3.78 (1H, m); 3.74 (1H, dd, J=3 and J=12); 3.87 (1H, dd, J=3 and J=12); 3.95-4.12 (3H, m); 4.70-4.83 (1H, m); 5.05-5.08 (2H, m); 7.16-7.21 (2H, m); 7.27-7.38 (5H, m); 7.56 (1H, dd, J=2 and J=14).

MS (ESI): 559.3.

8.iii. (RS)-3-[2-fluoro-4-((R)-5-hydroxymethyl-2-oxo-oxazolidin-3-yl)-phenoxymethyl]-pyrrolidine-1-carboxylic acid benzyl ester A solution of intermediate 8.ii (200 mg) in dioxane (1 mL) was treated with 6M HCl in dioxane (0.30 mL) at rt. The reaction mixture was stirred at rt for 2 h and concentrated to dryness. The residue was diluted in DCM, washed with sat. ac. NA CO$_3$ and worked up (DCM). The crude product was purified by FC (DCM/MeOH 98:2 to 96:4) to give 258 mg (81% yield) of a yellowish oil.

$^1$H NMR (DMSO$_{d6}$; δ ppm): 1.66-1.82 (1H, m); 1.96-2.10 (1H, m); 2.58-2.74 (1H, m); 3.14-3.26 (1H, m); 3.28-3.38 (1H, m); 3.39-3.61 (3H, m); 3.66 (1H, ddd, J=4, J=6 and J=13); 3.80 (1H, dd, J=6 and J=9); 3.94-4.08 (3H, m); 4.62-4.71 (1H, m); 5.05 (2H, s); 5.19 (1H, t, J=6); 7.18-7.21 (2H, m); 7.27-7.38 (5H, m); 7.57 (1H, dd, J=2 and J=14).

MS (ESI): 445.2.

8.iv. (R)-3-[3-fluoro-4-((RS)-1-pyrrolidin-3-ylmethoxy)-phenyl]-5-hydroxymethyl-oxazolidin-2-one This compound was prepared in 100% yield as a pinkish solid by hydrogenation of intermediate 8.iii (230 mg) over 10% Pd/C (72 mg) following the procedure of Example 6, step 6.viii.

MS (ESI): 311.3.

8.v. 1-cyclopropyl-6-fluoro-7-{(RS)-3-[2-fluoro-4-((R)-5-hydroxymethyl-2-oxo-oxazolidin-3-yl)-phenoxymethyl]-pyrrolidin-1-yl}-4-oxo-1,4-dihydro-quinoline-3-carboxylic acid This compound was prepared in 17% yield as a yellow solid, starting from intermediate 8.iv (67 mg), 7-chloro-1-cyclopropyl-6-fluoro-1,4-dihydro-4-oxo-3-quinolinecarboxylic acid boron diacetate complex (80 mg; prepared according to WO 88/07998) and DIPEA (36 lit), and following the procedure of Example 6, step 6.ix. The crude product was purified by chromatography (DCM/MeOH/AcOH 98:1:1 to 94:5:1) and the foamy residue was stirred in MeOH (1 mL).

$^1$H NMR (DMSO$_{d6}$; δ ppm): 1.10-1.34 (4H, m); 1.85-2.01 (1H, m); 2.14-2.28 (1H, m); 2.75-2.90 (1H, m); 3.48-3.60 (2H, m); 3.60-3.88 (6H, m); 4.05 (TH, t, J=9); 4.09-4.18 (2H, m); 4.63-4.72 (1H, m); 5.19 (1H, t, J=6); 7.09 (1H, d, J=8); 7.18-7.29 (2H, m); 7.58 (1H, dd, J=3 and J=14); 7.80 (1H, d, J=14); 8.58 (1H, s); 14.48 (1H, s).

MS (ESI): 556.3.

Example 9

1-cyclopropyl-6-fluoro-7-{(RS)-3-[2-fluoro-4-((R)-5-hydroxymethyl-2-oxo-oxazolidin-3-yl)-phenoxymethyl]-pyrrolidin-1-yl}-8-methoxy-4-oxo-1,4-dihydro-quinoline-3-carboxylic acid This compound was obtained as a yellow solid in 12% yield, starting from intermediate 8.iv (65 mg), 1-cyclopropyl-6,7-difluoro-1,4-dihydro-8-methoxy-4-oxo-3-quinolinecarboxylic acid boron diacetate complex (80 mg; prepared according to Sakurai et al., *Bioorg. Med. Chem. Lett.* (1998), 8, 2185-2190) and DIPEA (27 Pl) and following the procedure of Example 6, step 6.1x. The crude product was purified by chromatography (DCM/MeOH/AcOH 98:1:1 to 94:5:1) and the foamy residue was stirred in EA/Et$_2$O (2:1; 1.5 mL).

$^1$H NMR (DMSO$_{d6}$; δ ppm): 0.90-1.18 (4H, m); 1.76-1.93 (1H, m); 2.10-2.24 (1H, m); 2.70-2.81 (1H, m); 3.57 (3H, s); 3.56-3.83 (7H, m); 3.99-4.20 (4H, m); 4.62-4.73 (1H, m); 5.19 (1H, t, J=6); 7.18-7.29 (2H, m); 7.58 (1H, dd, J=3 and J 14); 7.68 (1H, d, J=14); 8.64 (1H, s); 15.13 (1H, s).

MS (ESI): 586.3.

Example 10

1-cyclopropyl-6-fluoro-7-{4-[2-fluoro-4-((R)-5-hydroxymethyl-2-oxo-oxazolidin-3-yl)-phenoxymethyl]-4-phosphonooxy-piperidin-1-yl}-4-oxo-1,4-dihydro-quinoline-3-carboxylic acid

10.i. 7-(4-{4-[5-(tert-butyldimethyl-silanyloxymethyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid benzyl ester Imidazole (67 mg) and TBDMSCl (162 mg) were added to a solution of intermediate 4.i (600 mg) in DMF (6 mL). The solution was stirred at rt for 6 h. The solvent was evaporated under reduced pressure and the residue was worked up (DCM) and purified by chromatography (DCM/MeOH; 95:5), affording 54 mg (75.6% yield) of a yellow solid.

$^1$H NMR (DMSO$_{d6}$; δ ppm): 0.03 (6H, s); 0.78 (9H, s); 1.10 (2H, m); 1.22 (2H, m); 1.70 (2H, m); 1.92 (2H, m); 3.2 (2H, m); 3.45 (2H, m); 3.70 (3H, m); 3.83-3.88 (1H, dd, J=2.6 and J=12); 3.89 (2H, s); 4.07 (1H, t, J=9); 4.73 (1H, m); 4.82 (1H, s); 5.26 (2H, m); 7.20 (2H, m); 7.28-7.58 (7H, m); 7.75 (1H, d, J=13.5); 8.46 (1H, s).

MS (ESI): 790.5.

10.ii. 7-(4-(bis-benzyloxy-phosphoryloxy)-4-{4-[(R)-5-(tert-butyl-dimethyl-silanyloxymethyl)-2-oxo-oxazolidin-3-yl]-2-fluoro-phenoxymethyl}-piperidin-1-yl)-1-cyclopropyl-6-fluoro-4-oxo-1,4-dihydro-quinoline-3-carboxylic acid benzyl ester A suspension of intermediate 10.i (523 mg) in DCM (4 mL) was sequentially treated with 4,5-dicyanoimidazole (140 mg) and dibenzyl N,N-diisopropylphosphoramidite (392 µl). After 1 h at rt, the reaction mixture was treated with 190 µl tert-butyl hydroperoxide (70% in water) and further stirred at rt for 1 h. The solvent was evaporated under reduced pressure and the residue was worked up (DCM) and purified by chromatography (DCM/MeOH; 97.5:2.5). The resulting solid (369 mg) was stirred in ether (5 mL), affording 287 mg (41% yield) of a yellow solid.

$^1$H NMR (DMSO$_{d6}$; δ ppm): 0.02 (6H, s); 0.77 (9H, m); 1.07 (2H, m); 1.19 (2H, dd, J=1.2 and J=6.4), 2.07 (2H, t broad, J=9); 2.29 (21H, d, J=135); 3.18 (2H, t, J=11); 3.49 (2H, m); 3.61 (1H, m); 3.73 (2H, m); 3.85 (1H, dd, J=2.6 and J=12); 4.07 (1H, t, J=9.1); 4.38 (2H, s); 4.73 (1H, m); 5.02 (4H, d, J=7.6); 5.26 (2H, S); 7.17 (2H, m); 7.42 (17H, m); 7.77 (1H, d, J=13.2); 8.46 (1H, s).

MS (ESI): 1050.3.

10.iii 7-{4-[4-((R)-5-acetoxymethyl-2-oxo-oxazolidin-3-yl)-2-fluoro-phenoxymethyl]-4-phosphonooxy-piperidin-1-yl}-1-cyclopropyl-6-fluoro-4-oxo-1,4-dihydro-quinoline-3-carboxylic acid benzyl ester A suspension of intermediate 10.ii (200 mg) in AcOH (1.5 mL) was treated with HBr (1 mL; 33% in AcOH) and stirred at rt for 2 h, The reaction mixture was poured into cold water (10 mL). After work-up (DCM), the residue was stirred in ether (30 mL). The resulting yellow solid was collected by filtration (144.5 mg; 95% yield).

MS (ESI); 798.1.

10.iv. 1-cyclopropyl-6-fluoro-7-{4-[2-fluoro-4-((R)-5-hydroxymethyl-2-oxo-oxazolidin-3-yl)-phenoxymethyl]-4-phosphonooxy-piperidin-1-yl}-4-oxo-1,4-dihydro-quinoline-3-carboxylic acid A solution of intermediate 10.iii (144.5 mg) in dioxane/MeOH/water (3 mL; 1:1:1) was treated with sodium acetate (29 mg) and hydrogenated over Pd/C 10% (10 mg) for 10 h at rt. The catalyst was filtered off and washed with water (5 mL). The filtrate was evaporated under reduced pressure and taken up in water (1 mL) and treated with 1N HCl (400 µl) until precipitation. The solid was collected by filtration, redissolved in MeOH (10 mL) and treated with K$_2$CO$_3$ (56.25 mg). After stirring the mixture at rt for 30 min, the solvent was evaporated under reduced pressure and the residue was dissolved in water (4 mL) and treated with 1N HCl (814 µl) until precipitation. The solid was collected by filtration, washed with water and dried under reduced pressure, affording 105 mg (82% yield) of yellow solid.

$^1$H NMR (DMSO$_{d6}$; δ ppm): 1.13-1.30 (4H, m); 1.95-2.11 (2H, t broad, J=10); 2.24 (2H, d, J=12.5); 3.59 (3H, t, J=10); 3.5-3.69 (3H, m); 3.74-3.87 (2H, m); 4.02 (1H, t, J=9); 4.31 (2H, m); 4.66 (1H, m); 5.17 (1H, m); 7.19 (2H, m); 7.56 (2H, m); 7.87 (1H, d, J=13.2); 8.63 (1H, s).

MS (ESI): 666.2.

Example 11

1-ethyl-6-fluoro-7-{4-[2-fluoro-4-((R)-5-hydroxymethyl-2-oxo-oxazolidin-3-yl)-phenoxymethyl]-piperidin-1-yl}-4-oxo-1,4-dihydro-quinoline-3-carboxylic acid This compound was prepared in analogy to Example 1, step 1.iv, starting from intermediate 2.iv (250 mg) and 7-chloro-1-ethyl-6-fluoro-1,4-dihydro-4-oxo-3-quinolinecarboxylic acid boron complex (280 mg; prepared according to WO 87/03595). The residue obtained after evaporation of the solvent under reduced pressure was dissolved in water (100 mL) and DCM/MeOH (500 mL; 9:1). The org. phase was dried over MgSO$_4$ and filtered. The filtrate was evaporated and stirred in DCM/MeOH (10 mL; 9:1). The yellow solid was collected by filtration (171 mg; 44% yield).

¹H NMR (DMSO_d6; δ ppm): 1.45 (3H, t, J=7); 1.57 (2H, dq, J=4.7 and J=9); 1.95 (2H, d, J=12.5); 2.01-2.09 (1H, m); 3.00 (2H, m); 3.62 (3H, dq, J=4 and J=13.2), 3.73-3.78 (1H, m); 3.80 (1H, dd, J=6.5 and J=9); 3.99-4.07 (3H, m); 4.49 (2H, q, J=7), 4.65 (1H, m); 7.16 (3H, m); 7.47-7.54 (1H, m); 7.88 (1H, d, J=13.8); 8.83 (1H, s).
MS (ESI): 558.2.

Example 12

7-(4-{4-[(R)-5-((S)-2-amino-propionyloxymethyl)-2-oxo-oxazolidin-3-yl]-2-fluoro-phenoxymethyl}-piperidin-1-yl)-1-cyclopropyl-6-fluoro-4-oxo-1,4-dihydro-quinoline-3-carboxylic acid hydrochloride 12.i. 1-cyclopropyl-6-fluoro-7-{4-[2-fluoro-4-((R)-5-hydroxymethyl-2-oxo-oxazolidin-3-yl)-phenoxymethyl]-piperidin-1-yl}-4-oxo-1,4-dihydro-quinoline-3-carboxylic acid benzyl ester A solution of the compound of Example 2 (600 mg) in DMF (10 mL) was treated with K₂CO₃ (155 mg) and BnBr (160 μl) and stirred at 80° C. for 24 h. The solvent was evaporated under reduced pressure and the residue was worked up (DCM). The residue was stirred in ether (100 mL) and the resulting crystals were collected by filtration affording 612 mg (90.6% yield) of an off-white solid.
¹H NMR (DMSO_d6; δ ppm): 1.08-1.27 (4H, m); 1.45-1.60 (2H, m); 1.88-2.05 (3H, m); 2.89 (2H, t, J=10.8); 3.50-3.57 (1H, m); 3.62-3.71 (4H, m); 3.78 (1H, dd, J=6.2 and J=8.8); 3.98 (2H, d, J=6.2); 4.03 (1H, t, J=8.8); 4.62-4.71 (1H, m); 5.17 (1H, t, J=5.9); 5.25 (2H, s); 7.19-7.22 (2H, m); 7.31-7.41 (3H, m); 7.43-7.49 (3H, m); 7.53-7.55 (1H, dd, J=2.0 and J=13.8); 7.75 (1H, d, J=13.8); 8.46 (1H, s).
MS (ESI): 660.3.

12.ii. 7-(4-{4-[(R)-5-((S)-2-tert-butoxycarbonylamino-propionyloxymethyl)-2-oxo-oxazolidin-3-yl]-2-fluoro-phenoxymethyl}-piperidin-1-yl)-1-cyclopropyl-6-fluoro-4-oxo-1,4-dihydro-quinoline-3-carboxylic acid benzyl ester This compound (307 mg; 81% yield) was obtained as a colorless solid in analogy to Example 4, step 4.ii, starting from intermediate 12.i (300 mg), Boc-L-Ala-OH (111 mg), EDC (113 mg) and DMAP (27 mg).
¹H NMR (DMSO_d6; δ ppm): 1.05-1.11 (2H, m); 1.17-1.26 (5H, m); 1.32 (9H, s); 1.52 (2H, m); 1.96 (3H, m); 2.90 (2H, t, J=11); 3.59-3.72 (3H, m); 3.81 (1H, dd, J=6.7 and J=9.7); 3.94-4.00 (3H, m); 4.12 (1H, t, J=9); 4.25 (1H, dd, J=4.7 and J=11); 4.40 (1H, dd, J=2.6 and J=12.3); 4.85-4.95 (1H, m); 5.26 (2H, s); 7.18-7.23 (2H, m); 7.26-7.46 (7H, m); 7.75 (1H, d, J=13.5); 8.45 (1H, s).
MS (ESI): 831.3.

12.iii. 7-(4-[4-[(R)-5-((S)-2-tert-butoxycarbonylamino-propionyloxymethyl)-2-oxo-oxazolidin-3-yl]-2-fluoro-phenoxymethyl]-piperidin-1-yl)-1-cyclopropyl-6-fluoro-4-oxo-1,4-dihydro-quinoline-3-carboxylic acid This compound (252 mg; 100% yield) was obtained as a yellow solid in analogy to Example 4, step 4.iii by hydrogenation of intermediate 12.ii (279 mg) over Pd/C (10 mg).
¹H NMR (DMSO_d6; δ ppm): 1.12-1.22 (5H, m); 1.26-1.36 (1H, m); 1.47-1.59 (2H, m); 1.92 (2H, d, J=12); 1.98-2.10 (1H, m); 2.99 (2H, t, J=12); 3.79 (4H, m); 3.97 (3H, d, J=7.6); 4.10 (1H, t, J=9); 4.26 (1H, dd, J=5.3 and J=12.6); 4.36-4.43 (1H, m); 4.84-4.96 (1H, m); 7.17-7.32 (3H, m); 7.52 (1H, d, J=12.9); 7.54 (1H, d, J=8.2); 7.88 (1H, d, J 13.5); 8.64 (1H, s).
MS (ESI): 741.3.

12.iv. 7-(4-{4-[(R)-5-((S)-2-amino-propionyloxymethyl)-2-oxo-oxozolidin-3 yl]-2-fluoro-phenoxymethyl}-piperidin-1-yl)-1-cyclopropyl-6-fluoro-4-oxo-1,4-dihydro-quinoline-3-carboxylic acid hydrochloride This compound (84 mg; 97% yield) was obtained as a yellow solid in analogy to Example 4, step 4.iv, starting from intermediate 12.iii (100 mg) and 5M HCl in dioxane (0.5 mL).
¹H NMR (DMSO_d6; δ ppm): 1.13-1.32 (4H, m); 1.36 (3H, d, J=7.3); 1.46-1.61 (2H, m); 1.92 (2H, d broad, J=12); 1.98-2.10 (1H, m); 2.99 (2H, t, J=12); 3.74-3.91 (5H, m); 3.98 (2H, d, J=6.4); 4.10-4.18 (1H, m); 4.35 (1H, dd, J=5.3 and J=12.3); 4.55 (1H, dd, J=2.6 and J=12.3); 4.96 (1H, m); 7.19-7.24 (2H, m); 7.52-7.58 (2H, m); 7.88 (1H, d, J=13.5); 8.47 (3H, m); 8.64 (1H, s).
MS (EST): 641.2.

Example 13

6-fluoro-7-{4-[2-fluoro-4-((R)-5-hydroxymethyl-2-oxo-oxazolidin-3-yl)-phenoxymethyl]-4-hydroxy-piperidin-1-yl}-4-oxo-1,4-dihydro-quinoline-3-carboxylic acid A solution of intermediate 1.iv (150 mg) in DMA (10 mL) was hydrogenated over 20% Pd(OH)₂/C (100 mg) for 5 days at 80° C. The reaction mixture was concentrated in vacuo, taken in DCM/MeOH 90:10 (50 mL) and stirred at rt for 30 min. The catalyst was filtered off and the filtrate concentrated in vacuo. The residue was taken in MeOH (0.2 mL) and EA (2 mL) was added. The suspension was stirred at rt for 30 min and filtered. The crystals were collected and dried in vacuo to give 48 mg (34% yield) of a yellow solid.
¹H NMR (DMSO_d6; δ ppm): 1.64-1.77 (2H, m); 1.82-1.98 (2H, m); 3.14-3.30 (2H, m); 3.38-3.59 (3H, m); 3.59-3.71 (1H, m); 3.78 (1H, dd, J=6 and J=9); 3.89 (2H, s); 4.03 (1H, t, J=9); 4.62-4.73 (1H, m); 4.84 (1H, s); 5.17 (1H, t, J=6); 7.16-7.23 (2H, m); 7.28 (1H, d, J=8); 7.51-7.60 (1H, m); 7.81 (1H, d, J=13); 8.79 (1H, s); 13.09 (1H, broad); 15.44 (1H, s).
MS (ESI): 546.2.

Example 14

6-fluoro-7-{4-[2-fluoro-4-((R)-5-hydroxymethyl-2-oxo-oxazolidin-3-yl)-phenoxymethyl]-4-hydroxy-piperidin-1-yl}-4-oxo-1,4-dihydro-[1,8]naphthyridine-3-carboxylic acid A solution of intermediate 3.i (110 mg) in DMA (10 mL) was hydrogenated over 10% Pd/C (35 mg) for 16 h at 80° C. The reaction mixture was concentrated in vacuo, taken in DCM/MeOH 90:10 (25 mL) and stirred at rt for 30 min. The catalyst was filtered off and the filtrate concentrated in vacuo. The residue was taken up in EA (2 mL), stirred at rt for 16 h and filtered. The crystals were collected and dried in vacuo to give 35 mg (34% yield) of a yellow solid.
¹H NMR (DMSO_d6; δ ppm): 1.62-1.92 (4H, m); 3.41-3.60 (3H, m); 3.60-3.69 (1H, m); 3.78 (1H, dd, J 6 and J=9); 3.86 (2H, s); 4.02 (1H, t, J=8); 4.22-4.37 (2H, m); 4.60-4.72 (1H, m); 4.95 (1H, broad); 5.18 (1H, broad); 7.13-7.23 (2H, m);

7.50-7.59 (1H, m); 8.01 (1H, d, J=14); 8.79 (1H, broad); 13.26 (1H, broad); 15.34 (1H, broad).

MS (ESI): 547.3.

BIOLOGICAL ASSAYS

In Vitro Assays

A) Antibacterial Activity of the Compounds of Formula I:

Experimental Methods:

These assays have been performed following the description given in "Methods for dilution Antimicrobial Susceptibility Tests for Bacteria that Grow Aerobically, 4th ed.; Approved standard: NCCLS Document M7-A4; National Committee for Clinical Laboratory Standards Villanova, Pa., USA, 1997". Minimal inhibitory concentrations (MICs; mg/l) were determined in cation-adjusted Mueller-Hinton Broth (BBL) by a microdilution method following NCCLS guidelines (National Committee for Clinical Laboratory Standards. Methods for Dilution Antimicrobial Susceptibility). The pH1 of the test medium was 7.2-7.3.

In the particular case wherein the compound to be tested is a compound of formula IPDc wherein at least one of $R^1$ and $R^2$ represents $OPO_3H_2$, then the test was carried out in the presence of human alkaline phosphatase (concentration: 1 U/mL).

In the particular case wherein the compound to be tested is a compound of formula $I_{PDG}$ wherein $R^1$ represents a group $OCOR^5$, then the test may be carried out in the presence of 50% human serum. However, this was not needed for the compounds of Examples 4 and 12 that already showed significant activity in the absence of human serum.

Results:

All the above Examples were tested against several Gram positive and Gram negative bacteria. Typical antibacterial spectra are given in Table 1 below (MIC in mg/l).

TABLE 1

| Example No. | S. aureus A798 | S. Pneumoniae 49619 | M. catarrhalis A894 |
| --- | --- | --- | --- |
| 3 | 0.25 | 0.125 | 0.5 |
| 7 | 1 | 0.25 | 0.063 |

Besides, the results shown in Table 2 have been obtained for the Example compounds corresponding to formula $I_D$ on S. aureus A798 (MIC in mg/l):

TABLE 2

| Example No. | S. aureus A798 |
| --- | --- |
| 1 | 0.25 |
| 2 | 0.25 |
| 3 | 0.25 |
| 6 | 1 |
| 7 | 1 |
| 8 | 0.125 |
| 9 | 1 |
| 11 | >16 |

TABLE 2-continued

| Example No. | S. aureus A798 |
| --- | --- |
| 13 | 2 |
| 14 | 4 |

In addition, the compound of Example 11 has a MIC of 8 mg/l against E. faecalis 29212 bacteria.

Moreover, in physiological environment (comprising phosphatases and esterases), the compounds of formula $I_{PDG}$ are rapidly converted into the corresponding compounds of formula $I_D$. Indeed:

the compounds of Examples 5 and 10, in the presence of human alkaline phosphatase, have MICs of respectively 0.25 and 0.5 mg/l against S. aureus A798, whereas the same compounds have MICs of respectively >16 mg/l and 16 mg/l against S. aureus A798 when the phosphatase is absent; and the compounds of Examples 4 and 12, even in the absence of human serum, each have a MIC of 0.5 mg/l against S. aureus A798.

B) Antibacterial Activity of the Compounds of Formula $I_{INT}$ Against Reference Strains of Clostridium difficile or Clostridium perfringens:

Experimental Methods:

Minimal inhibitory concentrations (MICs) were determined by a broth microdilution assay. Brucella broth supplemented with a final concentration of 0.5 mg/L of Vitamin $K_1$ and 5 mg/L hemin was used as the test medium. Briefly, stock solutions of the compounds were prepared in DMSO (5.12 mg mL), and 5 µl of a range of two-fold serial dilutions in 50% DMSO/50% $H_2O$ were dispensed into 96-well microtiter plates containing 45 µL supplemented Brucella broth and shaken for 5 min. To prepare the inocula 24 h old colonies of C. difficile grown on Brucella agar supplemented with 5% laked sheep blood, 5 µg of hemin/mL, and 1 µg of vitamin $K_1$/mL were suspended in supplemented Brucella broth and adjusted to a density matching 0.5 McFarland standard. 50 µL of a 50-fold dilution of this suspension was used to inoculate the wells of the 96-well plate resulting in approximately $10^4$ colony forming units (CFU) per well. The final DMSO concentration was 2.5%. The final concentration range was 0.03-16 µg/mL. The plates were incubated under anaerobic conditions for 48 h at 37° C. After incubation the plates were read in a plate reader at $OD_{595}$ (Ultramark, Biorad Laboratories). The MICs were initially read at the lowest concentration showing >90% of growth inhibition compared to control wells. Plates were also checked visually with the aid of a reading mirror, and MICs were confirmed by the absence of visual growth.

Results:

The compounds of Examples 1, 3 and 6 were tested in vitro for their activity to inhibit growth of three reference strains of C. difficile or Clostridium perfringens. The results obtained are summarised in Table 3 hereafter.

TABLE 3

| Compound tested | MIC regarding C. difficile ATCC 43596 (µg/mL) | MIC regarding C. difficile ATCC 9689 (µg/mL) | MIC regarding C. difficile NC 13366 (µg/mL) | MIC regarding C. perfringens DSM 756 (µg/mL) |
|---|---|---|---|---|
| Ciprofloxacin | 8 | 8 | >16 | 0.25 |
| Linezolid | 8 | 2 | 1 | 4 |
| Example 1 | 0.125 | 0.125 | 0.06 | ≦0.03 |
| Example 3 | 0.06 | 0.125 | 0.03 | ≦0.03 |
| Example 6 | 0.25 | 0.5 | 0.25 | 0.125 |

The compounds of Examples 1, 3 and 6 showed potent in vitro activity against the strains of C. difficile and C. perfringens tested. Strong activity was also observed against the quinolone-resistant hypervirulent strain NC13366. The compounds of Examples 1 and 3 were slightly more active than the compound of Example 6 and all of the compounds of Examples 1, 3 and 6 were clearly more active than ciprofloxacin and linezolid.

C) Antibacterial Activity of the Compound of Example 1 Against a Collection of Clinical Isolates of *Clostridium difficile*:

Experimental Methods:

The CLSI-recommended reference agar dilution method for anaerobes (M11-A6) was used for susceptibility testing. *Brucella* agar supplemented with 5% laked sheep blood, 5 µg of hemin/mL, and 1 µg of vitamin $K_1$/mL was the test medium. The test compounds were serially diluted and added to the molten supplemented agar. Growth controls were done on drug free plates. Prior to testing, all isolates were subcultured twice onto enriched *brucella* agar plates. Bacterial colonies were suspended in *brucella* broth. Standardization with a Vitek colorimeter was used to prepare each inoculum to the equivalent of a 0.5 McFarland standard, approximating $10^4$-$10^5$ CFU per spot after application with a Steers replicator. The plates were incubated under anaerobic conditions for 48 h at 37° C. The minimum inhibitory concentration (MIC) was the concentration that completely inhibited visible growth as compared to the drug-free control. All antibiotics were prepared and tested along with vancomycin and metronidazole as controls.

Results:

The compound of Example 1 was tested for its activity to inhibit growth of a collection of 209 diverse clinical isolates of *C. difficile* in vitro. The compound of Example 1 showed a MIC90 (minimal inhibitory concentration to inhibit the growth of 90% of strains or more) of 0.25 µg/mL, the MICs obtained ranging from 0.06 to 0.5 g/mL. It was on average more active than vancomycin, metronidazole and linezolid, which had MIC90s of 2, 1 and 8 µg/mL, respectively.

D) Antibacterial Activity of the Compound of Example 1 Against Aerobic Gram-Positive Bacteria:

Experimental Methods:

Minimal inhibitory concentrations (MICS) were determined by a broth microdilution assay following the guidelines of the Clinical Laboratory Standards Institute [CLSI, formerly NCCLS, 1971]. Briefly, stock solutions of the compounds were prepared in DMSO (5.12 mg/mL), serially diluted in cation-adjusted Mueller-Hinton Broth II (CaMHB), and dispensed in microtiter plates with the help of a Biomek 2000 pipeting robot (Beckman Coulter). The final DMSO concentration was 2.5% or below. Plates were inoculated to achieve a concentration of generally $3-6\times10^5$ CFU/mL. After incubation at 37° C. for 18-24 h, the plates were read in a plate reader at $OD_{595}$ (Ultramark, Biorad Laboratories). The MICs were initially read at the lowest concentration showing >90% of growth inhibition compared to control wells. Plates were also checked visually with the aid of a reading mirror, and the MICs were confirmed by the absence of visual growth.

Results:

The compound of Example 1 was tested against Gram-positive aerobic bacteria. The results obtained are summarised in Table 4 hereafter.

TABLE 4

| Strain | MIC measured for vancomycin (µg/mL) | MIC measured for ciprofloxacin (µg/mL) | MIC measured for linezolid (µg/mL) | MIC measured for the compound of Example 1 (µg/mL) |
|---|---|---|---|---|
| S. aureus ATCC 29213 | 1 | 0.25 | 2 | 0.25 |
| S. aureus A-798 (MRSA) | 1 | >16 | 2 | 0.25 |
| S. aureus ATCC 43300 (MRSA) | 1 | 0.25 | 2 | 0.25 |
| S. aureus S1 (LZD-R) | 1 | 0.25 | >32 | 1 |
| E. faecalis ATCC 29212 | 1 | 2 | 2 | 0.25 |
| E. faecalis H 4060 | >32 | >16 | 2 | 0.25 |
| E. faecalis H 6279 | >32 | >16 | 2 | 0.25 |
| E. faecalis H 6897 | >32 | >16 | 4 | 1 |
| E. faecalis H 7094 | >32 | >16 | 4 | 0.5 |
| E. faecalis H 7460 | >32 | >16 | 16 | 1 |
| E. faecium ATCC 19434 | 1 | 8 | 2 | 0.25 |
| E. faecium H 9070 | >32 | >16 | 2 | 1 |
| E. faecium H 7969 | >32 | >16 | 4 | 1 |
| E. faecium H 7966 | >32 | >16 | 1 | 0.5 |
| E. faecium H 7965 | >32 | >16 | 2 | 0.5 |
| E. faecium H 7937 | >32 | >16 | 1 | 0.25 |
| E. faecium A 962 | >32 | >16 | 4 | 0.5 |

TABLE 4-continued

| Strain | MIC measured for vancomycin (µg/mL) | MIC measured for ciprofloxacin (µg/mL) | MIC measured for linezolid (µg/mL) | MIC measured for the compound of Example 1 (µg/mL) |
|---|---|---|---|---|
| E. faecium A 949 | >32 | >16 | 2 | 1 |
| E. faecium L1 (LZD-R) | 0.5 | >16 | >32 | 2 |

In summary, the compound of Example 1 had potent in vitro activity against strains of Staphylococcus aureus, S. aureus MRSA, Enterococcus faecalis, and Enterococcus faecium. It was active against strains resistant to vancomycin, ciprofloxacin or linezolid.

E) Antibacterial Activity of the Compound of Example 1 Against Particular Anaerobic Bacterial Strains:

Using the experimental method described in assay D) above, the compound of Example 1 (Ex. 1) was tested in vitro for the ability to inhibit the growth of certain anaerobic bacteria that are known or suspected to play a role in the normal gut flora and in the maintenance of its role in protection against C. difficile overgrowth (hereafter collectively called "the commensal gut bacteria"). As references, the compound of Example 5 of WO 2005/058888 (R1) and ciprofloxacin (CP) were tested at the same time. The MICs thus obtained are shown in Table 5 hereafter.

TABLE 5

| | MIC [µg/mL] | | |
|---|---|---|---|
| Strains | R1 | Ex. 1 | CP |
| Clostridium difficile A-1179 NC 13366 | ≦0.06 | ≦0.06 | >32 |
| Fusobacterium necrophorum A-1260 DSM 20698 | 1 | 1 | 4 |
| Bacteroides ovatus A-991 ATCC 8483 | 8 | 16 | 16 |
| Bacteroides fragilis A-992 ATCC 25285 | 2 | 8 | 8 |
| Bacteroides thetaiotaomicron A-990 ATCC 29741 | 4 | 8 | 16 |
| Bacteroides vulgatus A-989 ATCC 8482 | 1 | 2 | 32 |
| Bacteroides fragilis A-502 T 7403 | 2 | 4 | 8 |
| Bacteroides fragilis A-348 T 8673 | 1 | 2 | 8 |
| Bacteroides fragilis A-217 B 6306 | 2 | 4 | 8 |
| Bacteroides fragilis A-501 B 8039 | 4 | 4 | 32 |
| Bacteroides fragilis A-294 T 9174 | 2 | 4 | 8 |
| Bacteroides fragilis A-293 B 2518 | 2 | 4 | 8 |
| Bacteroides fragilis A-260 T 9865 | 1 | 4 | 8 |
| Eubacterium limosum A-1259 DSM 20698 | 0.125 | 1 | 2 |
| Finegoldia magna A-1254 DSM 20470 | ≦0.06 | 0.25 | 2 |
| Bifidobacterium adolescentis A-1257 DSM 20083 | ≦0.06 | 0.5 | 2 |
| Bifidobacterium bifidum A-1258 DSM 20456 | 0.125 | 0.5 | 4 |
| Lactobacillus acidophilus A-1255 DSM 20079 | ≦0.06 | 0.5 | 32 |
| Lactococcus lactis A-1256 DSM 20069 | ≦0.06 | 0.5 | 1 |

In summary, the compound of Example 1 showed reduced activity regarding the commensal gut bacteria compared to C. difficile. For Bacteroides spp., which are important members of the human protective gut flora, the activity is 30 to 200 times lower. This selective activity offers the potential for selective killing of C. difficile in the gut while sparing important bacteria of the gut flora.

Besides, when compared to the compound of Example 5 of WO 2005/058888, the compound of Example 1 showed in most cases 2 to 4 times less activity against the tested Bacteroides spp., 4 times less activity against the Eubacterium limosum A-1259 or Finegoldia magna A-1254 strains, 4 to 8 times less activity against the tested Bifidobacterium spp. and 8 times less activity against the Lactobaciltis acidophihlis A-1255 and Lactococcus lactis A-1256 strains.

Therefore, when compared to the compound of Example 5 of WO 2005/058888 (R1), the compound of Example 1 was significantly less active against the commensal gut bacteria, indicating an advantage for selectively killing of C. difficile in the gut.

F) Effect of the Compound of Example 1 on C. difficile Toxin Production:

Experimental Methods:

Hypertoxigenic C. difficile strain NC13366 was grown anaerobically in supplemented Brucella broth for 24 h at 37° C. to a cell density of approximately $1 \times 10^8$ CFU/mL. Bacteria were washed by centrifugation and resuspended in the same volume of supplemented Brucella broth containing antibiotics at 1 and 8 µg/mL, respectively. The control contained no antibiotic. The cultures were further incubated anaerobically at 37° C. At day 5, culture supernatants were collected and assayed for toxin A and toxin B as described hereafter.

Toxin A was detected by Western Blotting using the NuPage Large Protein Analysis System (Invitrogen LP0001, according to kit instructions). The Western Breeze anti Mouse Immunodetection kit (Invitrogen WB7103) with anti CdTA mouse monoclonal antibodies (PCG4.1, Biodesign C70517M) was used.

C. difficile cytotoxic toxin (toxin B) was semiquantitatively detected by testing supernatants of C. difficile cultures for cell-rounding activity in CHO cells. CHO cells were seeded into 96-well flat bottom plates ($1 \times 10^5$ cells/well) and allowed to attach for 3 h. Appropriate dilutions of filter sterilized supernatants were added to the cells and further incubated at 37° C., in 5% $CO_2$. After 20 h of incubation cell rounding was determined using an inverted microscope. The toxin titer was defined as the highest serial 10-fold dilution of the supernatant resulting in >90% cell rounding.

Colony forming units (CFU) were determined by plating appropriate dilutions of test samples on supplemented *Brucella agar* and colony count after 48 h incubation at 37° C. under anaerobic conditions.

Results:

The outlook of a Western Blot plate to analyse toxin A production in supernatants of static high density cell cultures of *C. difficile* NC 13366 (a toxin-hyperproducing NAPI/027-type strain that caused outbreaks in hospitals with high mortality) is shown in FIG. 1.

The experimental method mentioned at the paragraph entitled "Experimental methods" was used to obtain the result shown in FIG. 1. At day 1 (DI), cultures were treated with either the compound of Example 1 (Ex. 1), vancomycin (V), metronidazole (M) at 1 and 8 μg/mL or left untreated (U); at day 5 $(1)_5$), the contents of toxin A in the supernatants were analysed and compared with those observed at D1 (see FIG. 1). In high density five day old stationary phase cultures of toxigenic *C. difficile*, the compound of Example 1 inhibited de novo toxin A production at concentrations of 1 and 8 μg/mL, i.e. at 2 and 16× the MIC (see FIG. 1). In contrast, metronidazole and vancomycin did not inhibit toxin A production under these conditions or did so only weakly.

Culture supernatants were also analyzed for the cytotoxic toxin B by using the cell-based cell-rounding assay mentioned in the paragraph entitled "Experimental methods". Activities of the supernatants of cultures treated with the compound of Example 1 were reduced to >90% compared to the untreated control. In contrast, activities of supernatants of vancomycin-treated cultures were not reduced (at 1 μg/mL) or reduced by only 30% (at 8 μg/mL).

In summary, the compound of Example 1 has the ability to stop efficiently the synthesis of *C. difficile* toxins A and B even in high density static cultures and in absence of killing, which is not the case for the vancomycin and metronidazole, the favoured drugs currently used for treatment of *C. difficile* infections.

G) Effect of the Compound of Example 1 on *C. difficile* Spore Formation:

Experimental Methods:

*C. difficile* A-1050 (ATCC 43596) was grown to logarithmic growth in supplemented *Brucella* broth resulting in turbidity matching McFarland 0.5 standard (6-7 h at 37° C. under anaerobic conditions). Cultures were diluted 1:50 in tubes containing 1 mL of supplemented *Brucella* broth containing the antibiotics at various concentrations in 2-fold dilution steps. Tubes were further incubated for 4 days at 37° C. under anaerobic conditions. The MIC was defined as the concentration that inhibited visible growth (turbidity) completely. 0.5×MIC was the highest concentration of drug allowing visible growth.

Assessment of colony forming units (CFUs) of total cells was performed by plating appropriate 10-fold dilutions of the cultures on Brazier's agar containing 4% egg yolk suspension and 1% lysed horse blood (Lab M). Colonies were counted after incubation at 37° C. for 48 h under anaerobic conditions. Spore counts were done by selectively killing of vegetative cells by treatment with 50% ethanol for 1 h at rt and subsequent CFU count on Braziers' agar as detailed above.

Results:

*C. difficile* is a spore forming organism and spores can persist for a long time in the hospital environment. Spores are very resistant to common disinfection procedures. Therefore spores play an important role in the transmission and persistence of *C. difficile* infections. Growing in vitro cultures of *C. difficile* were treated with various sub-MIC concentrations of the compound of Example 1, vancomycin or metronidazole and investigated for the effect on the production of spores after 4 days of anaerobic incubation at 37° C. (see the paragraph entitled "Experimental methods"). At a concentration representing 0.5× the MIC, treatment with compound of Example L resulted in low spore counts (<1% spores of total cell count). In contrast, untreated cultures and cultures treated with metronidazole or vancomycin at concentrations of 0.5× the MIC showed high sporulation rates (>90% spores of total cell counts). This indicates that the compound of Example 1 has the potential to reduce the production of spores during treatment of *C. difficile* infection more efficiently than vancomycin or metronidazole.

In Vivo Assay

Activity of an Invention Compound in the *C. difficile* Hamster Model:

Experimental Methods:

Golden Syrian hamsters were given a single injection of clindamycin phosphate (10 mg/kg s.c.), and a day later animals were infected by gavage with $10^5$ CFU of toxigenic *C. difficile* strain 10465. A fulminant colitis results in the majority (~95%) of animals and develops 1 to 2 days after the administration of *C. difficile*. Untreated, the colitis progresses rapidly and turns into severe colitis, hemorrhagic necrosis of the cecum and death. The compound of Example 1 was administered orally as a suspension at three dosage levels (10 mg/kg, 30 mg/kg and 100 mg/kg; n=10 per group). Vancomycin (50 mg/kg) was used as a control. Animals were treated once daily for 5 days and afterwards maintain under observation for an additional 21 days.

The animals were observed three times daily for morbidity and presence or absence of diarrhoea. The final endpoint of the study was survival. Animals judged to be in a moribund state [extended period of weight loss progressing to an emaciated state, anorexia for 24-48 h, prolonged lethargy (more than 3 days), signs of paralysis, skin erosions or trauma, hunched posture, distended abdomen] were euthanized by a single injection of sodium pentobarbital.

RESULTS

The therapeutic utility of the compound of Example 1 was tested using the protocol of the paragraph entitled "Experimental methods". All the infected untreated animals died between 2 and 5 days after infection whereas all animals treated with 10, 30 or 100 mg/kg of compound of Example 1 survived during the 5 day treatment period. At the lowest dose level, 40% of the animals survived the relapse phase of 21 days after treatment, whereas in the 30 and 100 mg/kg groups 80 and 300% of animals survived without relapse. Vancomycin with a 50 mg dose was used as a control. These results demonstrate that compound of Example 1 has a capacity to treat animals with *C. difficile* infections comparable to that of vancomycin.

The invention claimed is:
1. A compound of formula I

$$I$$

wherein
R¹ represents OH, OPO₃H₂ or OCOR⁵;
R² represents H, OH or OPO₃H₂;
A represents N or CR⁶;
R³ represents H or fluorine;
R⁴ is H, (C₁-C₃) alkyl or cycloalkyl;
R⁵ is the residue of a naturally occurring amino acid, or the enantiomer of a naturally occurring amino acid, or of dimethylaminoglycine;
R⁶ represents H, alkoxy or halogen; and
n is 0 or 1;
or a salt of the compound.

2. The compound according to claim 1, wherein n is 0.
3. The compound according to claim 1, wherein n is 1.
4. The compound according to claim 1, wherein A is CR⁶, R⁶ representing H or alkoxy.
5. The compound according to claim 1, wherein R³ is fluorine.
6. The compound according to claim 1, wherein R⁴ is cycloalkyl.
7. The compound according to claim 1, wherein the compound is:
   1-cyclopropyl-6-fluoro-7-{4-[2-fluoro-4-((R)-5-hydroxymethyl-2-oxo-oxazolidin-3-yl)-phenoxymethyl]-4-hydroxy-piperidin-1-yl}-4-oxo-1,4-dihydro-quinoline-3-carboxylic acid;
   1-cyclopropyl-6-fluoro-7-{4-[2-fluoro-4-((R)-5-hydroxymethyl-2-oxo-oxazolidin-3-yl)-phenoxymethyl]-piperidin-1-yl}-4-oxo-1,4-dihydro-quinoline-3-carboxylic acid;
   1-cyclopropyl-6-fluoro-7-{4-[2-fluoro-4-((R)-5-hydroxymethyl-2-oxo-oxazolidin-3-yl)-phenoxymethyl]-4-hydroxy-piperidin-1-yl}-4-oxo-1,4-dihydro-[1,8]naphthyridine-3-carboxylic acid;
   7-(4-{4-[(R)-5-((S)-2-amino-propionyloxymethyl)-2-oxo-oxazolidin-3-yl]-2-fluoro-phenoxymethyl}-4-hydroxy-piperidin-1-yl)-1-cyclopropyl-6-fluoro-4-oxo-1,4-dihydro-quinoline-3-carboxylic acid;
   1-cyclopropyl-6-fluoro-7-{4-[2-fluoro-4-((R)-2-oxo-5-phosphonooxymethyl-oxazolidin-3-yl)-phenoxymethyl]-4-hydroxy-piperidin-1-yl}-4-oxo-1,4-dihydro-quinoline-3-carboxylic acid;
   1-cyclopropyl-6-fluoro-7-{(R)-3-[2-fluoro-4-((R)-5-hydroxymethyl-2-oxo-oxazolidin-3-yl)-phenoxymethyl]-3-hydroxy-pyrrolidin-1-yl}-4-oxo-1,4-dihydro-quinoline-3-carboxylic acid;
   1-cyclopropyl-6-fluoro-7-{(S)-3-[2-fluoro-4-((R)-5-hydroxymethyl-2-oxo-oxazolidin-3-yl)-phenoxymethyl]-3-hydroxy-pyrrolidin-1-yl}-4-oxo-1,4-dihydro-quinoline-3-carboxylic acid;
   1-cyclopropyl-6-fluoro-7-{(R)-3-[2-fluoro-4-((R)-5-hydroxymethyl-2-oxo-oxazolidin-3-yl)-phenoxymethyl]-3-hydroxy-pyrrolidin-1-yl}-8-methoxy-4-oxo-1,4-dihydro-quinoline-3-carboxylic acid;
   1-cyclopropyl-6-fluoro-7-{(S)-3-[2-fluoro-4-((R)-5-hydroxymethyl-2-oxo-oxazolidin-3-yl)-phenoxymethyl]-3-hydroxy-pyrrolidin-1-yl}-8-methoxy-4-oxo-1,4-dihydro-quinoline-3-carboxylic acid;
   1-cyclopropyl-6-fluoro-7-{(R)-3-[2-fluoro-4-((R)-5-hydroxymethyl-2-oxo-oxazolidin-3-yl)-phenoxymethyl]-pyrrolidin-1-yl}-4-oxo-1,4-dihydro-quinoline-3-carboxylic acid;
   1-cyclopropyl-6-fluoro-7-{(S)-3-[2-fluoro-4-((R)-5-hydroxymethyl-2-oxo-oxazolidin-3-yl)-phenoxymethyl]-pyrrolidin-1-yl}-4-oxo-1,4-dihydro-quinoline-3-carboxylic acid;
   1-cyclopropyl-6-fluoro-7-{(R)-3-[2-fluoro-4-((R)-5-hydroxymethyl-2-oxo-oxazolidin-3-yl)-phenoxymethyl]-pyrrolidin-1-yl}-8-methoxy-4-oxo-1,4-dihydro-quinoline-3-carboxylic acid;
   1-cyclopropyl-6-fluoro-7-{(S)-3-[2-fluoro-4-((R)-5-hydroxymethyl-2-oxo-oxazolidin-3-yl)-phenoxymethyl]-pyrrolidin-1-yl}-8-methoxy-4-oxo-1,4-dihydro-quinoline-3-carboxylic acid;
   1-cyclopropyl-6-fluoro-7-{(S)-3-[2-fluoro-4-((R)-5-hydroxymethyl-2-oxo-oxazolidin-3-yl)-phenoxymethyl]-4-phosphonooxy-piperidin-1-yl}-4-oxo-1,4-dihydro-quinoline-3-carboxylic acid;
   1-ethyl-6-fluoro-7-{-4-[2-fluoro-4-((R)-5-hydroxymethyl-2-oxo-oxazolidin-3-yl)-phenoxymethyl]-piperidin-1-yl}-4-oxo-1,4-dihydro-quinoline-3-carboxylic acid;
   7-(4-{4-[(R)-5-((S)-2-amino-propionyloxymethyl)-2-oxo-axazolidin-3-yl]-2-fluoro-phenoxymethyl}-piperidin-1-yl)-1-cyclopropyl-6-fluoro-4-oxo-1,4-dihydro-quinoline-3-carboxylic acid;
   6-fluoro-7-{-4-[2-fluoro-4-((R)-5-hydroxymethyl-2-oxo-oxazolidin-3-yl)-phenoxymethyl]-4-hydroxy-piperidin-1-yl}-4-oxo-1,4-dihydro-quinoline-3-carboxylic acid;
   6-fluoro-7-{4-[2-fluoro-4-((R)-5-hydroxymethyl-2-oxo-oxazolidin-3-yl)-phenoxymethyl]-4-hydroxy-piperidin-1-yl}-4-oxo-1,4-dihydro-[1,8]naphthyridine-3-carboxylic acid;
or a pharmaceutically acceptable salt thereof.

8. The compound according to claim 1, including 1-cyclopropyl-6-fluoro-7-{4-[2-fluoro-4-((R)-5-hydroxymethyl-2-oxo-oxazolidin-3-yl)-phenoxymethyl]-4-hydroxy-piperidin-1-yl}-4-oxo-1,4-dihydro-quinoline-3-carboxylic acid, or a pharmaceutically acceptable salt thereof.

9. A pharmaceutical composition comprising the compound according to claim 1 and at least one therapeutically inert excipient.

10. A method of treating a bacterial infection in a patient, which comprises administering to said patient a therapeutically effective dose of the compound according to claim 1.

11. A method of treating a bacterial infection in a patient, which comprises administering to said patient a therapeutically effective dose of the compound according to claim 8.

12. A method of treating an intestinal disease which is caused by *Clostridium difficile, Clostridium perfringens* or *Staphylococcus aureus* bacteria comprising the administration of an effective amount of a compound of formula $I_{INT}$

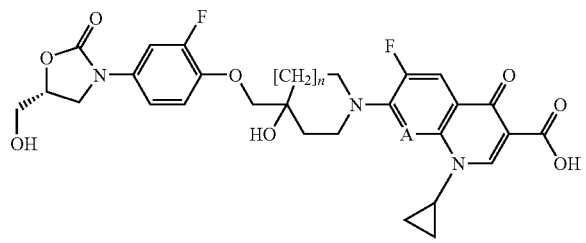

wherein
A is N or CH; and
n is 0 or 1;
or of a pharmaceutically acceptable salt of the compound, to a patient in need thereof for a duration sufficient to treat the intestinal disease.

13. The method of claim 12, wherein the compound of formula $I_{INT}$ is:
1-cyclopropyl-6-fluoro-7-{4-[2-fluoro-4-((R)-5-hydroxymethyl-2-oxo-oxazolidin-3-yl)-phenoxymethyl]-4-hydroxy-piperidin-1-yl}-4-oxo-1,4-dihydro-quinoline-3-carboxylic acid;
1-cyclopropyl-6-fluoro-7-{-4-[2-fluoro-4-((R)-5-hydroxymethyl-2-oxo-oxazolidin-3-yl)-phenoxymethyl]-4-hydroxy-piperidin-1-yl}-4-oxo-1,4-dihydro-[1,8]naphthyridine-3-carboxylic acid;
1-cyclopropyl-6-fluoro-7-{3-[2-fluoro-4-((R)-5-hydroxymethyl-2-oxo-oxazolidin-3-yl)-phenoxymethyl]-3-hydroxy-pyrrolidin-1-yl}-4-oxo-1,4-dihydro-quinoline-3-carboxylic acid;
or a pharmaceutically acceptable salts thereof.

14. The method of claim 12, wherein the compound of formula $I_{INT}$ is 1-cyclopropyl-6-fluoro-7-{4-[2-fluoro-4-((R)-5-hydroxymethyl-2-oxo-oxazolidin-3-yl)-phenoxymethyl]-4-hydroxy-piperidin-1-yl}-4-oxo-1,4-dihydro-quinoline-3-carboxylic acid; or a pharmaceutically acceptable salt thereof.

15. The method of claim 12, wherein the intestinal disease is caused by *Clostridium difficile* bacteria.

16. The method of claim 15, wherein the intestinal disease is caused by a toxin producing strain of *Clostridium difficile* bacteria.

17. The method of claim 12, wherein the concentration of vancomycin-resistant enterococci in the gut does not increase over the duration.

18. The method of claim 12, wherein the concentration of vancomycin-resistant enterococci in the gut is reduced over the duration.

* * * * *